(12) United States Patent
Vial et al.

(10) Patent No.: US 6,972,343 B1
(45) Date of Patent: Dec. 6, 2005

(54) QUATERNARY BIS-AMMONIUM SALT PRECURSORS AND THEIR USES AS PRODRUGS HAVING AN ANTIPARASITIC ACTIVITY

(75) Inventors: Henri Vial, Montpellier (FR); Marie-Laure Ancelin, St. Jean de Cuculles (FR); Valerie Vidal, Montpellier (FR); Michele Calas, Montpellier (FR); Jean-Jacques Bourguignon, Hipsheim (FR); Eric Rubi, Montigny les Cornelles (FR)

(73) Assignee: CNRS, Paris Cedex (FR)

( * ) Notice: Subject to any disclaimer, the term of this patent is extended or adjusted under 35 U.S.C. 154(b) by 29 days.

(21) Appl. No.: 10/031,486

(22) PCT Filed: Jul. 21, 2000

(86) PCT No.: PCT/FR00/02122

§ 371 (c)(1),
(2), (4) Date: Feb. 5, 2002

(87) PCT Pub. No.: WO01/05742

PCT Pub. Date: Jan. 25, 2001

(30) Foreign Application Priority Data

Jul. 21, 1999 (FR) ............................................ 99 09471

(51) Int. Cl.[7] ............................................ C07C 233/05
(52) U.S. Cl. ........................ 564/154; 544/60; 544/110; 548/202; 549/473; 558/251
(58) Field of Search ........................ 564/154; 558/251; 549/473; 548/202; 544/60, 110

(56) References Cited

U.S. PATENT DOCUMENTS

| 3,131,220 A | 4/1964 | Zirkle |
| 3,278,537 A | 10/1966 | Hagiwara |

FOREIGN PATENT DOCUMENTS

| FR | 2 751 967 A | 2/1998 |

OTHER PUBLICATIONS

Calahorra et al, Tetrahedron, vol 51, No. 35, pp 9713–9728, 1995.*
Marti, Josep et al; "Introduction To A Rational Design of Chiral Thiazolium Salts"; Tetrahedron Lett; 1993; 34 (3), 521–4; XP002141680; p. 524; Figure 4;.
Chemical Abstracts; vol. 55, No. 12; Jun. 12, 1961; Columbus, Ohio, US; R.R. Mitchell; "The Intestinal Absorption Of Some Omega–Haloalkylamines And Their Quaternary Analogs" column 11643g; XP002141681; Abstract; & J. Pharmacol. Exptl. Therap., vol. 131, 1961, pp. 334–340.

F. Lopez–Calahorra et al; "Use Of 3, 3'–Polymethylene-Bridged Thazolium Salts Plus Bases As Catalysts of Benzoin Condensation And Its Mechanism Implications: Proposal Of A New Mechanism In Aprotic Conditions" Heterocycles; vol. 37, No. 3; 1994; pp. 1570–1597;XP002141688; pp. 1595–pp. 1596.

D.D. Libman et al; "Somes Bisquaternary Salts", Journal of the Chemical Society; 1952; pp. 2305–2307; XP002141689; Letchworth GB; p. 2306.

* cited by examiner

Primary Examiner—Shailendra Kumar
(74) Attorney, Agent, or Firm—Nixon & Vanderhye P.C.

(57) ABSTRACT

The invention concerns drug precursors with antimalarial effect, characterised in that it consists in quaternary bis-ammonium salts of general formula (I) wherein A and A', identical or different, are respectively either a group A1 and A'1 of formula (1) wherein n=2 to 4; R'1 is hydrogen, C1–C5 alkyl, optionally substituted by an aryl, a hydroxy, an alkoxy, wherein the alkyl comprises 1 to 5 C, or aryloxy and W is halogen or a nucleofuge group; or a group A2 which represents formyl-CHO, or acetyl-COCH3. B and B', identical or different, represent respectively either the group B1 and B'1, if A and A' respectively represent A1, A'1, B1, B'1 representing a group R1 which has the same definition as R'1 above, but cannot be a hydrogen atom; or respectively the groups B2 and B'2, if A and A' represent A2, B2 or B'2 being the group R1 as defined above, or a group of formula (2) wherein —Ra is RS— or RCO—, wherein R is a C1–C6 alkyl, substituted if required, a phenyl or benzyl, wherein the phenyl is substituted if required, the latter being optionally substituted; R2 is hydrogen, C1–C5 alkyl, or a —CH2-COO— (C1–C5)alkyl group; and R3 is hydrogen, C1–C5 alkyl or alkenyl, substituted if required, a phosphate, an alkoxy wherein the alkyl is a C1–C3 alkyl, or aryloxy; or an alkyl (or arylcarbonyloxy; or R2 and R3 form together a cycle with 5 or 6 C; R and R3 can be bound to form a cycle. ± represents: either a single bond when A and A' represent A1 and A'1: or when A and A' represent A2, and B2 and B'2 Represent (3) either, when A and A' are —CHO or —COCH3 and B2 and B'2 are R1, a group of formula (4) or a group of formula (5) wherein (a) represents a bond towards Z and (b) a bond towards the nitrogen atom. Z is a C9–C21 alkyl, if required with insertion of one or several bonds, and/or one or several heteroatoms O and/or S and/or several aromatic cycles, and the pharmaceutically acceptable salts of said compounds. Said precursors and cyclized thiazolium derivatives are useful as antiparasitic medicines in particular antimalarial and antibabesiosis.

27 Claims, 6 Drawing Sheets

Figure 1:
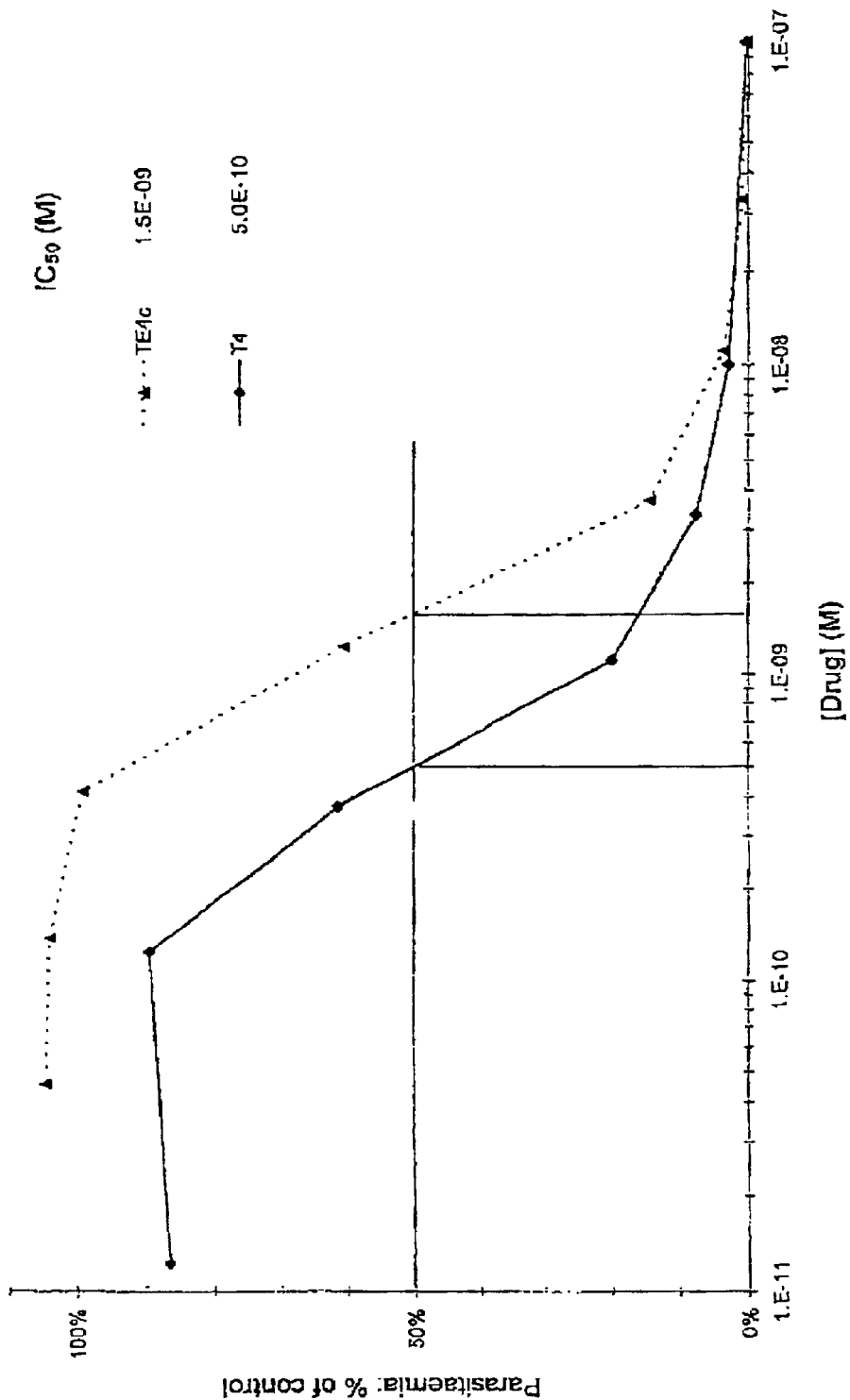

QUATERNARY BIS-AMMONIUM SALT PRECURSORS AND THEIR USES AS PRODRUGS HAVING AN ANTIPARASITIC ACTIVITY

This application is the U.S. National Phase of International PCT/FR00/02122 filed 21 Jul. 2000, which designated the U.S.

The invention relates to precursors of quaternary bis-ammonium salts and their uses as prodrugs presenting, in particular, an anti-parasitic, and more especially an anti-malarial action.

The geographic spread of parasitic diseases, and more especially malaria, is considerable.

More than 100 countries are affected at present by malaria and more than 2 billion people are exposed to the risk of infection, i.e. nearly half of the world's population (for the malaria situation in the world, see Butler et al, Nature, 1997, 386, 535–540).

The recrudescence of chemically resistant strains of *Plasmodium falciparum* (species deadly to man) in Asia, in Africa and in Latin America is more pertinent than ever and considerably limits the efficacy of the available treatments.

It is therefore considered urgent to have available effective anti-malarial medicaments.

In previous work, some co-inventors of the present Patent Application developed an original pharmacological model capable of preventing the reproduction of the parasite. The compounds synthesized have a quaternary bis-ammonium type structure with a spacer arm, one of the most studied compounds being constituted by 1,16-hexadecamethylene bis-(N-methylpyrrolidinium), corresponding to the formula

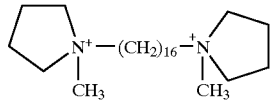

This compound is hereafter called G25 (FR patent 2 751 967).

If such compounds are of considerable interest taking into account the cures that they lead to in vivo, without relapse, their action by oral route has, however, proven to be inferior by a factor of at least 100 to that observed by intramuscular route.

Continuation of the work of the inventors to research new compounds presenting an increased efficacy when they are administered by oral route has led them to study a strategy based on the development of neutral prodrugs, a priori more easily absorbed, capable of generating in vivo the active drug which is present in ionized form.

Surprisingly, this work has made it possible to develop very effective prodrugs of quaternary bis-ammonium salts, endowed with a high anti-parasitic action, which are easily absorbed, generating in vivo active drugs the bioavailability of which is high.

The invention therefore aims to provide new neutral derivatives, with a high anti-malarial action, which can also be administered by oral route, as well as ionized metabolites generated in vivo.

It also relates to a process for synthesizing these prodrugs.

According to yet another aspect, the invention relates to the advantageous use of the properties of these prodrugs for the development of active ingredients of medicaments which can be used for the treatment of parasitic diseases, and in particular malaria and babesiosis in animals or humans.

The precursors of drugs with an anti-malarial action according to the invention are characterized in that they are products capable of generating quaternary bis-ammonium salts and that they correspond to general formula (I)

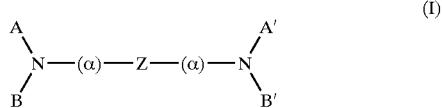

in which

A and A' are identical to or different from one another and represent either, an $A_1$ and $A'_1$ group respectively of formula

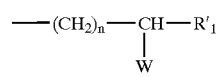

where n is an integer from 2 to 4; $R'_1$ represents a hydrogen atom, a C1 to C5 alkyl radical, optionally substituted by an aryl (in particular a phenyl radical), a hydroxy, an alkoxy radical, in which the alkyl radical comprises from 1 to 5 C, or aryloxy (in particular phenoxy); and W represents a halogen atom chosen from chlorine, bromine or iodine, or a nucleofuge group, such as the tosyl $CH_3$—$C_6H_4$—$SO_3$, mesityl $CH_3$—$SO_3$, $CF_3$—$SO_3$, $NO_2$—$C_6H_4$—$SO_3$ radical, or an $A_2$ group which represents a formyl —CHO, or acetyl —$COCH_3$ radical, B and B' are identical to or different from one another and represent either the $B_1$ and $B'_1$ groups respectively, if A and A' represent $A_1$ and $A'_1$ respectively, $B_1$ and $B'_1$ representing an $R_1$ group which has the same definition as $R'_1$ above, but which cannot be a hydrogen atom, or the $B_2$ and $B'_2$ groups respectively, if A and A' represent $A_2$, $B_2$ or $B'_2$ being the $R_1$ group as defined above, or a group of formula

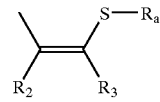

in which —Ra represents an RS— or RCO— group, where R is a linear, branched or cyclic C1 to C6 alkyl radical, in particular C1 to C5, optionally substituted by one or more hydroxy or alkoxy or aryloxy groups or an amino group and/or a —COOH or COOM group, where M is a C1 to C3 alkyl; a phenyl or benzyl radical, in which the phenyl radical is optionally substituted by at least one C1 to C5 alkyl or alkoxy radical, these being optionally substituted by an amino group, or by a nitrogenous or oxygenous heterocycle, a —COOH or —COOM group; or a —$CH_2$— heterocycle group, with 5 or 6 elements, nitrogenous and/or oxygenous; $R_2$ represents a hydrogen atom, a C1 to C5 alkyl radical, or a —$CH_2$—COO-alkyl (C1 to C5) group; and $R_3$ represents a hydrogen atom, a C1 to C5 alkyl or alkenyl radical, optionally substituted by —OH, a phosphate group, an alkoxy radical, in which the alkyl radical is C1 to C3, or aryloxy, or an alkyl (or aryl) carbonyloxy group; or also $R_2$ and $R_3$ together form a ring with 5 or 6 carbon atoms; R and $R_3$ can be linked to form a ring of 5 to 7 atoms (carbon, oxygen, sulphur)

α represents
either a single bond, when A and A' represent $A_1$ and $A'_1$: or when A and A' represent $A_2$, i.e. a —CHO or —COCH$_3$ group, and $B_2$ and $B'_2$ represent

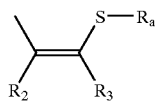

either, when A and A' represent $A_2$ and $B_2$ and $B'_2$ represent $R_1$, a group of formula

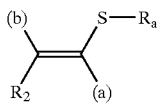

or a group of formula

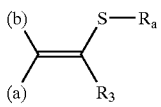

in which (a) represents a bond towards Z and (b) a bond towards the nitrogen atom, Z represents a C6 to C21 in particular C13 to C21 alkylene radical, optionally with insertion of one or more multiple bonds, and/or of one or more O and/or S heteroatoms, and/or one or more aromatic rings, and the pharmaceutically acceptable salts of these compounds.

Except where otherwise specified, "aryl" and "aromatic" as used to define the products of the invention designate a phenyl or any ring, or heterocycle, having an aromatic characteristic such as the pyridine, oxazole, thiazole rings, "alkenyl" designates an alkyl comprising one or more unsaturations, "amino group" designates —NH$_2$ or dialkyl ($C_1$–$C_3$) amino, and multiple bond designates an unsaturation (double or triple bond) between 2 carbon atoms.

A preferred group of compounds according to the invention is constituted by the haloalkylamines, precursors of quaternary bis-ammonium salts, which correspond to general formula (II)

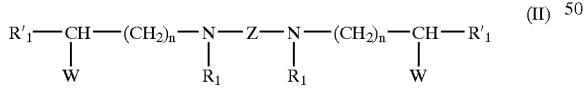

In these compounds, $R_1$, $R'_1$, W, n and Z are as defined 20 above.

In a preferred family of these compounds Z represents a C13 to C21 alkylene radical.

In the preferred derivatives, Z represents a —(CH$_2$)$_{16}$— group.

In a sub-group of this family, $R_1$ is advantageously a methyl radical.

In another sub-group, $R_1$ is a methyl radical and $R'_1$ is either a hydrogen atom, or a methyl radical, and W is a chlorine atom.

Particularly preferred compounds are chosen from N,N'-dimethyl-N,N'-(5-chloropentyl)-1,16-hexadecanediamine dihydrochloride, or N,N'-dimethyl-N,N'-(4-chloropentyl)-1,16-hexadecanediamine dihydrochloride.

Another preferred group of compounds according to the invention is constituted by precursors of thiazolium and correspond to general formula (III)

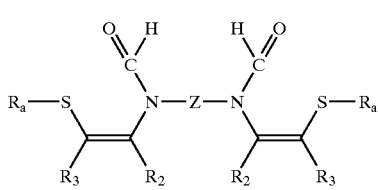

in which $R_a$, $R_2$, $R_3$, and Z are as defined above.

In a preferred sub-group of this family, $R_a$ represents an RCO— radical. Particularly preferred compounds are chosen from N,N'-diformyl-N,N'-di[1-methyl-2-S-thiobenzoyl-4-methoxybut-1-enyl]-1,12-diaminododecane (designated in the examples by TE4c), N,N'-diformyl-N,N'-di[1-methyl-2-S-(p-diethylaminomethylphenyl-carboxy)thio-4-methoxybut-1-enyl]-1,12-diaminododecane (TE4f), N,N'-diformyl-N,N'-di[1-methyl-2-S-(p-morpholinomethylphenylcarboxy)-thio-4-methoxybut-1-enyl]-1,12-diaminododecane (TE4g), N,N'-diformyl-N,N'-di[1-methyl-2-S-thiobenzoyl-4-methoxybut-1-enyl]-1,16-diaminohexadecane (TE8), N,N'-diformyl-N,N'-di[1(2-oxo-4,5-dihydro-1,3-oxathian-4-ylidene)ethyl]1,12-diaminododecane (TE3)

In another preferred sub-group, $R_a$ represents an RS-radical. Particularly preferred compounds are chosen from N,N'-diformyl-N,N'-di[1-methyl-2-tetrahydrofurfuryl-methyldithio-4-hydroxybut-1-enyl]-1,12-diaminododecane (TS3a), N,N'-diformyl-N,N'-di[-methyl-2-propyl-dithio-4-hydroxybut-1-enyl]-1,12-diaminododecane (TS3b), N,N'-diformyl-N,N'-di[1-methyl-2-benzyl-dithio-4-hydroxybut-1-enyl]-1,12-diaminododecane (TS3c), N,N'-diformyl-N,N'-di[1-methyl-2-(2-hydroxyethyl)-dithio-4-hydroxybut-1-enyl]-1,12-diaminododecane (TS3d)

N,N'-diformyl-N,N'-di[1-methyl-2-propyldithio-4-methoxybut-1-enyl]-1,12-diaminododecane (TS4b), N,N'-diformyl-N,N'-di[1-methyl-2-propyldithio-ethenyl]-1,12-diaminododecane (TS6b).

Another preferred group of compounds according to the invention is also constituted by precursors of thiazolium salts which correspond to general formula (IV)

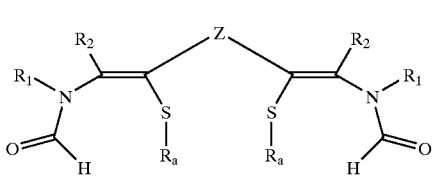

in which $R_a$, $R_2$, $R_1$ and Z are as defined above.

Particularly preferred compounds are chosen from 2,17-(N,N'-diformyl-N,N'-dimethyl)diamino-3,16-S-thio-p-methoxybenzoyl-6,13-dioxaoctadeca-2,16-diene (TE9), 2,17(N,N'-diformyl-N,N'-dibenzyl)diamino-3,16-S-thio-p-methoxybenzoyl-6,13-dioxaoctadeca-2,16-diene (TE10), ethyl 3,18(N,N'-diformyl-N,N'-dimethyldiamino-4,17-S-thiobenzoyl-eicosa-3,17-dienedioate (TE12), ethyl 3,18-(N,N'-diformyl-N,N'-dibenzyl)diamino-4,17-S-thiobenzoyl-eicosa-3,17-dienedioate (TE13).

Another preferred group of compounds according to the invention is again constituted by precursors of thiazolium salts which correspond to general formula (V)

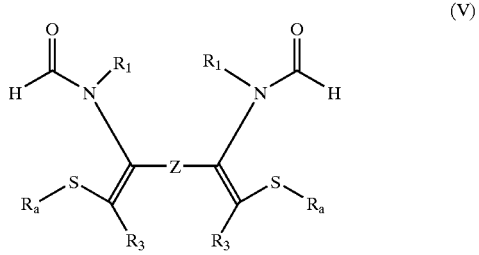

(V)

in which $R_a$, $R_3$, $R_1$ and Z are as defined above.

Particularly preferred compounds are chosen from 2,15-(N,N'-diformyl-N,N'-dimethyl)diamino-1,16-S-thiobenzoyl-hexadeca-1,15-diene (TE15), 2,15-(N,N'-diformyl-N,N'-dibenzyl)diamino-1,16-S-thiobenzoyl-hexadeca-1,15-diene (TE16).

The precursors according to the invention are presented optionally in the form of salts. The hydrochlorides, the citrates, the tartrates, the maleates or the lactates can be mentioned as examples.

The invention also relates to the cyclized derivatives generated from the precursors of thiazolium described above.

These derivatives correspond to general formula (VI)

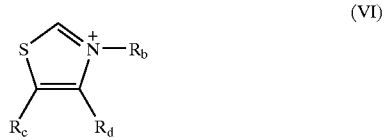

(VI)

in which $R_b$ represents $R_1$ or T, T representing the group of formula

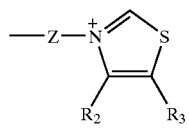

$R_d$ represents $R_2$ or P, P representing the group of formula

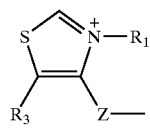

$R_c$ represents $R_3$ or U, U representing the group of formula

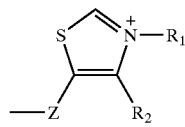

$R_1$, $R_2$, $R_3$ and Z being as defined above, it being understood that $R_b$=T if $R_c$=$R_3$ and $R_d$=$R_2$; $R_d$=P if $R_c$=$R_3$ and $R_b$=$R_1$; and $R_c$=U if $R_b$=$R_1$, and $R_d$=$R_2$.

In accordance with the invention, the precursors of thiazolium of general formula (III) to (IV) defined above can be obtained by a process characterized in that it comprises the reaction in basic medium of a thiazole derivative of formula (VI), as illustrated in the examples In an advantageous fashion, in order to obtain $R_a$=RCO—, a thiazolium derivative of formula (VI) is reacted with an RCOR' derivative, where R is as defined above and R' is a halogen atom, and in order to obtain $R_a$=RS— the said thiazolium derivatives of formula (VI) are reacted with a thiosulphate derivative $RS_2O_3Na$.

The N-duplicated series of thiazolium salts is obtained, generally speaking, by reacting a thiazole derivative suitably substituted with an alkyl dihalide under reflux in an organic solvent.

The duplicated C series on the C5 carbon of the thiazole ring, which comprises an oxygen in the Z chain, is obtained by reacting a thiazole derivative of general formula (VII)

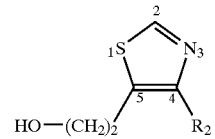

(VII)

with an alkane dihalide, in basic medium, then the addition of $R_1X$, the reaction medium being advantageously taken to reflux in an organic solvent, in particular alcohol such as ethanol, for a length of time sufficient to obtain the quaternization of the nitrogen atom of the thiazole by fixation of $R_1$.

The opening of the obtained thiazolium ring is then carried out in basic medium, and by the action either of R—COCl, or of R—$S_2O_3Na$.

In order to obtain the C-duplicated series on the 5 carbon of the thiazole ring and not comprising oxygen in the Z chain, a compound of structure

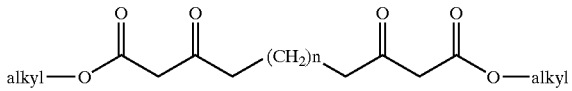

is firstly synthesized by reacting an alkyl acetoacetate with NaH, in an organic solvent, at a temperature of the order of 0° C., then the compound formed with for example an alkyllithium is alkylated and a dihalogenoalkane is added to the reaction medium.

The compound obtained is dibrominated by adding bromine at a temperature of the order of 0° C., then thioformamide is added and the reaction mixture is left under reflux for several days. By adding $R_1X$ to the reaction mixture, then subjecting it to reflux for several days, a thiazolium is obtained the opening of which is then carried out in basic medium.

In order to obtain the C-duplicated series on the C4 carbon of the thiazole ring, and not comprising
chain, a Z(CO—CH$_2$X)$_2$ compound is reacted with CH(=S)NH$_2$, then R$_1$X is added.

The invention also relates to a process for obtaining haloalkylamines corresponding to general formula (II). This process is characterized by the alkylation of an aminoalcohol of formula

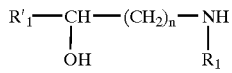

by an α, ω-dihalide of alkyl X—Z—X, which leads to a bisaminoalcohol treated with a compound capable of releasing the W group.

The alkylation of the aminoalcohol is carried out for example with an alkyl α, ω-dichloride, of formula Cl—Z—Cl, in ethanol, in the presence of diisopropylethylamine, the aminoalcohol being in a large excess in relation to the halide (approximately 2.1/1). The bis-aminoalcohol obtained is then treated with a compound capable of releasing W, which can be for example thionyl chloride, in dichloromethane, in order to obtain a compound in which W represents Cl, or with the chloride of a sulphonic acid, for example tosyl chloride in order to obtain a compound in which W=CH$_3$—C$_6$H$_4$—SO$_3$—.

Study of the action of the products of the invention vis-à-vis parasites, and in particular Plasmodium, has shown that they have a strong action in vitro.

Thus, the values of IC$_{50}$ (50% inhibitory concentration of the parasite) are of the order of nM vis-à-vis *P. falciparum*.

The invention therefore relates to the advantageous use of the properties of the precursors of the invention and of cyclized thiazolium compounds for the development of pharmaceutical compositions.

The pharmaceutical compositions of the invention are characterized in that they contain an effective quantity of at least one precursor as defined above, or of at least one cyclized compound of thiazolium, in combination with an inert pharmaceutical vehicle or at least one cyclized thiazolium compound.

The invention also relates to the use of at least one of the said precursors, or at least one of the said cyclised thiazolium compounds, to manufacture medicaments for the treatment of infectious diseases, in particular malaria or babesiosis in man or animals.

These compositions optionally contain the active ingredients of other medicaments. Their combination with other anti-malarial drugs (such as lysosomotropic agents, atovaquone, antifolic or antifolinic agents, or artemisinin or one of its derivatives) for reasons of pharmacological synergy or to avoid resistance can in particular be mentioned.

They can also be used to advantage in combination with compounds facilitating their assimilation.

The pharmaceutical compositions of the invention can be administered in different forms, more especially by oral or injectable route or also by rectal route.

For administration by oral route, tablets, pills, pressed tablets, gelatin capsules, drops can in particular be used.

Other forms of administration include solutions injectable by intravenous, sub-cutaneous or intramuscular route, developed from solutions which are sterile or can be sterilized. It can also concern suspensions or emulsions.

Suppositories can also be used for other forms of administration.

The compositions of the invention are particularly suitable for the treatment of infectious diseases in man and animals, in particular malaria or babesiosis.

By way of example, the dose which can be used in man corresponds to the following doses: therefore 0.02 to 80 mg/kg in one or more doses is for example administered to the patient.

The invention also relates to the biological reagents containing as active ingredients, the precursors of thiazolium defined above.

These reagents can be used as references or standards in studies of possible anti-parasitic action.

Other characteristics and advantages of the invention will become clear in the examples which follow relative to obtaining precursors of thiazolium and in the study of their anti-parasitic activity. In these examples, reference will be made to FIGS. 1 to 8, which represent respectively, FIG. 1, the anti-malarial action of a precursor of thiazolium (designated by TE4c in the examples), and corresponding thiazolium (T4) as a function of the concentration of drug, according to the Desjardins test, (Desjardins R. E. et al, Antimicrob. Agents Chemother. 1979, 16, 710–718), FIGS. 2 and 3, the pharmacokinetics in the mouse of a precursor of thiazolium according to the invention at a low dose (designated by TE4c in the examples) after administration by ip and per os route, FIG. 4, a semi-logarithmic representation of the pharmacokinetics in the mouse of precursors and of a drug according to the invention, after administration by ip and per os route, FIGS. 5A and 5B, the pharmacokinetics of a precursor and of a drug of the invention in the mouse after administration by ip and per os route, FIGS. 6 and 7, the pharmacokinetics in the mouse after administration by ip per os route, and FIGS. 8A and 8B, the pharmacokinetics of precursors of the invention in the monkey.

In the different diagrams given in the examples, the substituents have the meanings given above, X represents a counter ion, Me=methyl, Et=ethyl, Ph or φ=C$_6$H$_5$—,
DMSO=dimethylsulphoxide, THF=tetrahydrofuran, Bu=butyl.

I. SYNTHESIS OF TRIAZOLIUM PRECURSORS
A. Synthesis of Disulphide Prodrugs (TS):

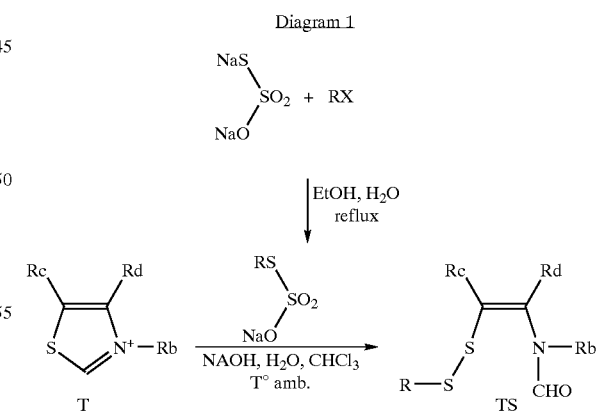

Diagram 1

General Operating Method:
a) Synthesis of the Alkyl Thiosulphate (Bunte Salt)

30 mmoles of halogen derivative are dissolved in 15 mL of ethanol and 5 g (30 mmol) of sodiumthiosulphate in a minimum amount of water are added. The mixture is heated to reflux for 5 days. The solution is evaporated to dryness and the crude residue obtained is used without purification.

b) Synthesis of the Disulphide Prodrug 2.6 mmoles of thiazolium drug are dissolved in 10 mL of water. 0.6 g of NaOH then 10 mL of $CHCl_3$ are added and the mixture is stirred vigorously for 10 mn. 7.8 mmoles of the alkyl thiosulphate obtained previously is then added dropwise and the mixture is stirred at ambient temperature for 2 hours. The organic phase is separated and washed with a 5% HCl solution. It is then neutralized with a solution of $NaHCO_3$, dried with $Na_2SO_4$ and concentrated. The oil obtained is purified on silica gel eluting with a $CH_2Cl_2$/MeOH mixture (9.5/0.5).

1. Synthesis of N,N'-diformyl-N,N'-di[1-methyl-2-tetrahydro-furfurylmethyldithio-4-hydroxybut-1-enyl]-1,12-diaminododecane (TS3a)

a) Preparation of Tetrahydrofurfurylmethyl Thiosulphate

The preparation is carried out according to §a of the general operating method above, starting from tetrahydrofurfuryl chloride.

NMR $^1$H (250 MHz, $D_2O$): δ 4.04 (m, 1H, $CH_2$—CH—O), 3.61 (m, 2H, —$CH_2$—O), 3.00 (m, 2H, S—$CH_2$—CH), 1.47–1.88 (m, 4H, —CH—$CH_2$—$CH_2$—)

b) Synthesis of TS3a

According to §b of the general operating method above, starting from T3 (see its preparation further on) and Bunte salt obtained previously, a yellowish oil is obtained.

NMR $^1$H (250 MHz, $CDCl_3$): δ 7.88–7.99 (2s, 2H, CHO), 3.95 (m, 2H, O—CH—$CH_2$), 3.7 (m, 8H, —$CH_2$—OH+CH—$OCH_2$—$CH_2$), 3.32 (m, 4H, S—$CH_2$—), 2.8 (m, 8H, N—$CH_2$—+=C—$CH_2$), 1.64–1.94 (m, 18H, —N—$CH_2$—$CH_2$—+CH—$CH_2$—$CH_2$—+$CH_3$—C=), 1.26 (m, 16H, $(CH_2)_8$).

2. Synthesis of N,N'-diformyl-N,N'-di[1-methyl-2-propyl-dithio-4-hydroxybut-1-enyl]-1,12-diaminododecane (TS3b)

a) Preparation of Propyl Thiosulphate

The preparation is carried out according to §a of the general operating method above, starting from propyl bromide.

NMR $^1$H (250 MHz, $D_2O$): δ 0.74 (t, 2H, —$CH_3$), 1.51 (m, 2H, —$CH_2CH_2CH_3$), 2.86 (t, 2H, S—$CH_2$—$CH_2$—)

b) Preparation of TS3b

According to §b of the general operating method above, starting from T3 (see its preparation further on) and the Bunte salt obtained previously, a yellowish oil is obtained.

NMR $^1$H (250 MHz, $CDCl_3$): δ 7.91–7.99 (2s, 2H, CHO), 3.8 (m, 4H, —$CH_2$—OH), 3.39 (m, 4H, S—$CH_2$—), 2.91 (t, 4H, =C—$CH_2$), 2.62 (t, 4H, N—$CH_2$—), 2.00 (d, 6H, $CH_3$—C=), 1.64 (m, 8H, —N—$CH_2$—$CH_2$—+—S—$CH_2$—$CH_2$—), 1.26 (m, 16H, —$(CH_2)_8$—), 0.97 (t, 6H, —S—$CH_2$—$CH_2$—$CH_3$)

3. Synthesis of N,N'-diformyl-N,N'-di[1-methyl-2-benzyl-dithio-4-hydroxybut-1-enyl]-1,12-diaminododecane (TS3c)

a) Preparation of Benzyl Thiosulphate

The preparation is carried out according to §a of the general operating method above, starting from benzyl bromide.

NMR $^1$H (250 MHz, $D_2O$): δ 4.13 (s, 2H, —$CH_2$—), 7.23 (m, 5H, —ArH).

b) Preparation of TS3c

According to §b of the general operating method above, starting from T3 (see its preparation further on) and the Bunte salt obtained previously, a yellowish oil is obtained.

NMR $^1$H (250 MHz, $CDCl_3$): δ 7.91–7.99 (2s, 2H, CHO), 3.89 (s, 4H, S—$CH_2$—Ph), 3.73 (t, 4H, $CH_2$—OH), 3.40 (t, 4H, N—$CH_2$—), 2.75 (t, 4H, =C—$CH_2$), 1.96 (s, 6H, $CH_3$—C=), 1.52 (m, 4H, —N—$CH_2$—$CH_2$—), 1.25 (m, 16H, —$(CH_2)_8$—).

4. Synthesis of N,N'-diformyl-N,N'-di[1-methyl-2-(2-hydroxyethyl)dithio-4-hydroxybut-1-enyl]-1,12-diaminododecane (TS3d)

a) Preparation of 2-hydroxyethyl Thiosulphate

The preparation is carried out according to §a of the general operating method above, starting from 2-chloroethanol.

NMR $^1$H (250 MHz, $D_2O$): δ 3.32 (t, 2H, S—$CH_2$), 3.98 (t, 2H, —$CH_2$—OH)

b) Preparation of TS3d

According to §b of the general operating method above, starting from T3 (see its preparation further on) and the Bunte salt obtained previously, an oil is obtained.

NMR $^1$H (250 MHz, $CDCl_3$): δ 7.91–7.87 (2s, 2H, CHO), 4.61 (m, 4H, —S—$CH_2$—$CH_2$—OH), 3.75 (m, 4H, =C—$CH_2$—$CH_2$—OH), 3.33 (m, 4H, S—$CH_2$—), 2.87 (t, 4H, =C—$CH_2$), 2.78 (t, 4H, N—$CH_2$—), 1.95 (d, 6H, $CH_3$—C=), 1.45 (m, 4H, —N—$CH_2$—$CH_2$—), 1.20 (m, 16H, —$(CH_2)_8$—)

5. Synthesis of N,N'-diformyl-N,N'-di[1-methyl-2-propyldithio-4-methoxybut-1-enyl]-1,12-diaminododecane (TS4b)

According to §b of the general operating method above, starting from T4 (see its preparation further on) and propyl thiosulphate, a yellowish oil is obtained.

NMR $^1$H (250 MHz, $CDCl_3$): δ 7.91 and 7.99 (2s, 2H, CHO), 3.8 (m, 4H, —$CH_2$—OH), 3.39 (m, 4H, S—$CH_2$—), 2.91 (t, 4H, =C—$CH_2$), 2.62 (t, 4H, N—$CH_2$—), 2.00 (s, 6H, $CH_3$—C=), 1.64 (m, 9H, —N—$CH_2$—$CH_2$—+—S—$CH_2$—$CH_2$—), 1.26 (m, 16H, —$(CH_2)_8$—), 0.97 (t, 6H, —S—$CH_2$—$CH_2$—$CH_3$).

6. Synthesis of N,N'-diformyl-N,N'-di[-methyl-2-propyldithio-ethenyl]-1,12-diaminododecane (TS6b)

According to §b of the general operating method above, starting from T6 (see its preparation further on) and of propyl thiosulphate, a yellowish oil is obtained.

NMR $^1$H (250 MHz, $CDCl_3$): δ 8.02 (s, 2H, CHO), 6.03 (s, 2H, =C—H), 3.47 (t, 4H, N—$CH_2$—), 2.69 (t, 4H, S—$CH_2$—), 1.95 (s, 6H, $CH_3$—C=), 1.72 (m, 4H, —S—$CH_2$—$CH_2$—), 1.59 (m, 4H, —N—$CH_2$—$CH_2$—), 1.26 (m, 16H, —$(CH_2)_8$—), 0.99 (t, 6H, —S—$CH_2$—$CH_2$—$CH_3$).

TABLE 1

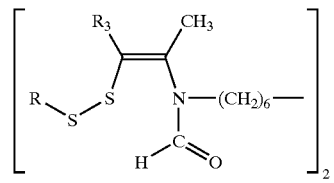

| compounds | $R_3$ | R | Yield % | $IC_{50}$ (nM) |
|---|---|---|---|---|
| TS3a | —$CH_2$—$CH_2$—OH | —$CH_2$—(tetrahydrofuran-2-yl) | 60 | 1.0 |

TABLE 1-continued

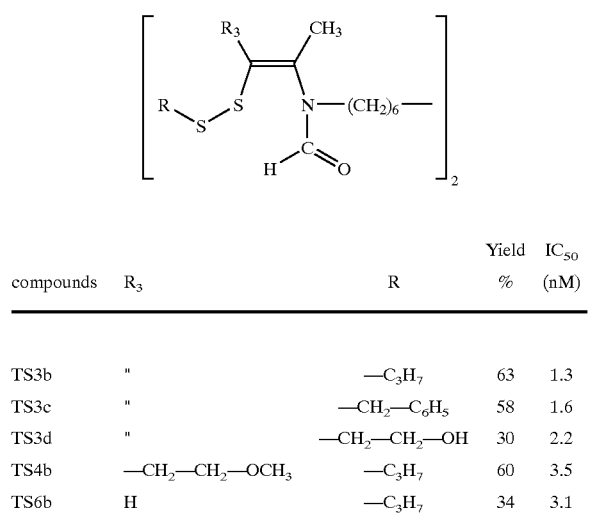

| compounds | $R_3$ | R | Yield % | $IC_{50}$ (nM) |
|---|---|---|---|---|
| TS3b | " | —$C_3H_7$ | 63 | 1.3 |
| TS3c | " | —$CH_2$—$C_6H_5$ | 58 | 1.6 |
| TS3d | " | —$CH_2$—$CH_2$—OH | 30 | 2.2 |
| TS4b | —$CH_2$—$CH_2$—$OCH_3$ | —$C_3H_7$ | 60 | 3.5 |
| TS6b | H | —$C_3H_7$ | 34 | 3.1 |

B. Synthesis of Thioester Prodrugs (TE):

Diagram 2

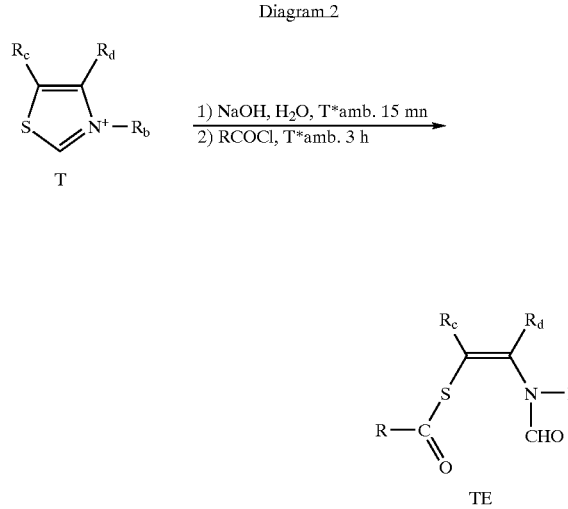

General Operating Method:

3.15 mmoles of thiazolium salt are suspended in 10 mL of water and 0.75 g (6 equivalents) of NaOH are added. The solution obtained is left under magnetic stirring for 15 min. Then, 9.6 mmoles (3 equivalents) of acid chloride in solution in 20 mL of $CHCl_3$ are added dropwise and the reaction mixture is stirred at ambient temperature for 3 hours. The organic phase is separated, washed with water saturated with NaCl then dried over $MgSO_4$ and concentrated in an evaporator. The residue obtained is purified on silica gel (eluent $CH_2Cl_2$/MeOH: 95/5).

1. Synthesis of Thioester Derivatives of the N Duplicated Series (Compounds TE4a–j, TE3 and TE8):

TABLE 2

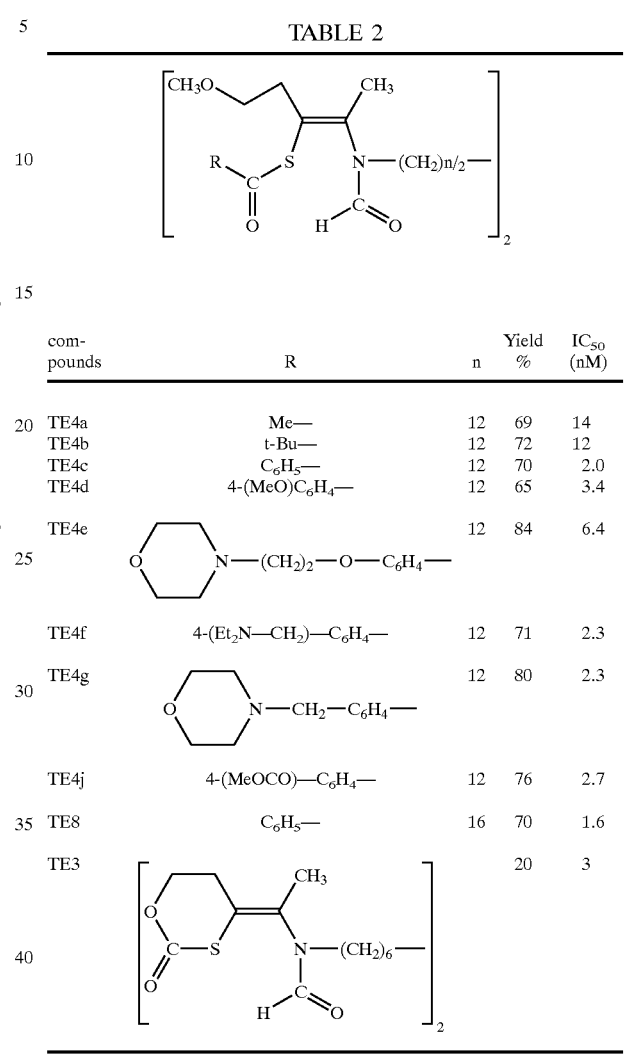

| compounds | R | n | Yield % | $IC_{50}$ (nM) |
|---|---|---|---|---|
| TE4a | Me— | 12 | 69 | 14 |
| TE4b | t-Bu— | 12 | 72 | 12 |
| TE4c | $C_6H_5$— | 12 | 70 | 2.0 |
| TE4d | 4-(MeO)$C_6H_4$— | 12 | 65 | 3.4 |
| TE4e | (morpholino)N—$(CH_2)_2$—O—$C_6H_4$— | 12 | 84 | 6.4 |
| TE4f | 4-($Et_2$N—$CH_2$)—$C_6H_4$— | 12 | 71 | 2.3 |
| TE4g | (morpholino)N—$CH_2$—$C_6H_4$— | 12 | 80 | 2.3 |
| TE4j | 4-(MeOCO)—$C_6H_4$— | 12 | 76 | 2.7 |
| TE8 | $C_6H_5$— | 16 | 70 | 1.6 |
| TE3 | (cyclic carbonate structure) | | 20 | 3 |

1.1. Synthesis of N,N'-diformyl-N,N'-di[1-methyl-2-S-thiobenzoyl-4-methoxybut-1-enyl]-1,12-diaminododecane (TE4c)

According to the operating method described above, starting from T4 and using benzoyl chloride, a white powder is obtained (Yield=70%)

NMR $^1$H (250 MHz, $CDCl_3$): δ 7.90–7.36 (m, 12H, CHO+ArH), 3.52–3.29 (m, 8H, $CH_3OCH_2$—, N—$CH_2$—), 3.30 (s, 6H, $CH_3O$), 2.75 (t, 4H, $CH_3OCH_2CH_2$—), 2.06 (s, 6H, $CH_3$—C=), 1.57–1.09 (m, 20H, —$(CH_2)_{10}$—).

MS $ES^+$: m/e 725 ($[M+H]^+$, 100).

1.2. Synthesis of N,N'-diformyl-N,N'-di[1-methyl-2-S-(p-diethylaminomethylphenylcarboxy)-thio-4-methoxybut-1-enyl]-1,12-diaminododecane (TE4f)

a) Synthesis of α-diethylamino-paratoluic Acid 1 g (1 equivalent) of α-chloroparatoluic acid and 1.22 mL (2 equivalents) of diethylamine are placed in solution in 30 mL of acetonitrile. The reaction mixture is taken to reflux for 48 hours. The solvent is evaporated off under vacuum and the residue is purified by chromatography on silica gel column (CH$_2$Cl$_2$/MeOH 60/40 then pure MeOH). The product is obtained in the form of a white powder after precipitation from hexane. (Yield=63%).

NMR $^1$H (250 MHz, DMSOD$_6$): δ 7.84 and 7.29 (2d, 2x2H, ArH), 3.50 (s, 2H, N—CH$_2$—Ar), 2.40 (q, 4H, N(CH$_2$—CH$_3$)$_2$), 0.9 (t, 6H, N(CH$_2$—CH$_3$)$_2$).

MS ES$^+$: m/e 208 ([M+H]$^+$, 100).

b) Synthesis of α-diethylaminoparatoluic Acid Chloride 0.3 g (1.45 mmol) of α-diethylaminoparatoluic acid are placed in 10 mL of CHCl$_3$ and 0.32 mL of SOCl$_2$ are added. The solution is taken to reflux for 12 hours The solvent is evaporated off under vacuum and the residue is recrystallized from ethyl ether. 323 mg of product is obtained, in the form of its hydrochloride (Yield=85%).

MS ES$^+$: m/e 226 ([M+H]$^+$, 100), 228 ([M+H]$^+$, 30).

c) Synthesis of TE4f (in the Form of the Hydrochloride)

0.7 g (0.95 mmol) of T4 are suspended in 10 mL of water and 0.23 g (5.71 mmol) of NaOH are added. The solution obtained is left under stirring for 15 min. Then, 0.75 g (2.86 mmol) of α-diethylaminoparatoluic acid chloride in solution in 20 mL of CHCl$_3$ and 0.4 mL (2.86 mmol) of triethylamine are added dropwise. The reaction mixture is stirred at ambient temperature for 4 hours The organic phase is separated, washed with water and dried over MgSO$_4$ and concentrated with a rotary evaporator. The oil obtained is purified by chromatography on silica gel column (CH$_2$Cl$_2$/MeOH 95/5 then pure MeOH). The hydrochloride is obtained by bubbling gaseous HCl through a solution of the base in ether at 0° C. for 3 hours This salt is obtained in the form of a foamy precipitate. (Yield=54%).

NMR $^1$H of the free base: (250 MHz, CDCl$_3$): δ 8.00–7.48 (m, 10H, CHO+ArH), 3.62–3.37 (m, 12H, CH$_3$OCH$_2$—CH$_2$—+N—CH$_2$—Ar), 3.35 (s, 6H, CH$_3$O), 2.80 (t, 4H, N—CH$_2$—), 2.50 (q, 8H, N(CH$_2$—CH$_3$)$_2$), 2.15 (s, 6H, CH$_3$—C=), 1.50–1.12 (m, 20H, —(CH$_2$)$_{10}$—), 1.08 (t, 12H, N(CH$_2$—CH$_3$)$_2$).

MS ES$^+$: m/e 448.5 ([M+2H]$^+$, 100).

1.3. Synthesis of N,N'-diformyl-N,N'-di[1-methyl-2-S-(p-morpholino-methylphenylcarboxy)-thio-4-methoxybut-1-enyl]-1,12-diaminododecane (TE4g)

a) Synthesis of α-morpholinoparatoluic Acid 4.04 g (1 equivalent) of α-chloroparatoluic acid and 4.13 g (2 equivalents) of morpholine are placed in solution in 150 mL of toluene. The reaction mixture is taken to reflux for 24 hours The morpholine hydrochloride is eliminated by warm filtration through a Buchner. The product crystallizes from the filtrate at ambient temperature. After filtration and drying, 3.63 g of product is obtained in the form of a white powder (Yield=70%).

NMR $^1$H (250 MHz, DMSOD$_6$): δ 7.84 and 7.37 (2d, 2x2H, ArH), 3.53 (t, 4H, CH$_2$OCH$_2$), 3.48 (s, 2H, Ar—CH$_2$—), 2.31 (t, 4H, CH$_2$—N—CH$_2$—).

MS ES$^+$: m/e 222 ([M+H]$^+$, 100).

b) Synthesis of α-morpholinoparatoluic Acid Chloride 2.33 g of α-morpholinoparatoluic acid are placed in 30 mL of CH$_{2Cl2}$ and 3.76 g of SOCl$_2$ are added. The not very homogenous solution is taken to reflux for 48 hours The white precipitate obtained is filtered, washed with CH$_2$Cl$_2$ and dried. 2.65 g of product is obtained (Yield=70%).

NMR $^1$H (250 MHz, DMSOD$_6$): δ 7.97 and 7.78 (2d, 2x2H, ArH), 4.40 (s, 2H, Ar—CH$_2$—), 3.86 (m, 4H, CH$_2$OCH$_2$—), 3.18 (m, 4H, CH$_2$—N—CH$_2$—).

MS ES$^+$: m/e 240 ([M+H]$^+$, 100), 242 ([M+H]$^+$, 30).

c) Synthesis of TE4 g (in the Form of the TE4go Dioxalate or TE4gt Ditartrate Salt)

1.08 g of T4 are suspended in 10 mL of water and 0.37 g (6 equivalents) of NaOH are added. The solution obtained is left under stirring for 15 min. Then, 1.15 g (3 equivalents) of the hydrochloride of α-morpholinoparatoluic acid chloride in solution in 20 mL of CHCl$_3$ and 0.42 g of triethylamine are added dropwise. The reaction mixture is stirred at ambient temperature for 3 hours The organic phase is extracted then dried over MgSO$_4$ and concentrated with a rotary evaporator. The residue obtained is taken up in ether and water. The organic phase is extracted, washed twice with water then dried over MgSO$_4$ and concentrated. The oil obtained is taken up in a minimum amount of ether and an ethereal solution containing 0.41 g of oxalic acid is added. A white precipitate forms immediately (TE4go: Yield=80%). A other sample of oil (7.7 g)is placed in solution with an aqueous solution (1N) containing 2 equivalents of tartaric acid (+). The solution is evaporated to dryness. The residue is dissolved in ethanol, the solution is again evaporated. A solid foam (TE4gt, Pf: 82–85° C.) is obtained.

Characterization of the Free Base:

NMR $^1$H (250 MHz, CDCl$_3$): δ 7.90–7.36 (m, 10H, CHO+ArH), 3.69 (t, 8H, CH$_2$OCH$_2$—), 3.52–3.32 (m, 12H, CH$_3$OCH$_2$CH$_2$—+N—CH$_2$—Ar), 3.30 (s, 6H, CH$_3$O), 2.77 (t, 4H, N—CH$_2$—), 2.42 (t, 8H, —CH$_2$—N—CH$_2$—), 2.09 (s, 6H, CH$_3$—C=), 1.57–1.09 (m, 20H, —(CH$_2$)$_{10}$—).

MS ES$^+$: m/e 462 ([M+2H]$^+$, 100), m/e 923 ([M+H]$^+$, 10).

1.4. Synthesis of N,N'-diformyl-N,N'-di[1-methyl-2-S-(p-phthaloyl)-thio-4-methoxybut-1-enyl]-1,12-diaminododecane (TE4j)

According to the operating method described above, starting from T4 and using p-methoxycarbonylbenzoyl chloride, a white powder is obtained (Yield=76%).

NMR $^1$H (250 MHz, CDCl$_3$): δ 7.90–7.36 (m, 10H, CHO+ArH), 3.97 (s, 6H, CH$_3$OCO), 3.57–3.35 (m, 8H, CH$_3$OCH$_2$CH$_2$—), 3.30 (s, 6H, CH$_3$O), 2.82 (t, 4H, N—CH$_2$—), 2.13 (s, 6H, CH$_3$—C=), 1.58–1.17 (m, 20H, —(CH$_2$)$_{10}$—).

MS ES$^+$: m/e 421 ([M+2H]$^{++}$, 20). 841 ([M+H]$^+$, 100).

1.5. Synthesis of N,N'-diformyl-N,N'-di[1-methyl-2-S-thiobenzoyl-4-methoxybut-1-enyl]-1,16-diaminohexadecane (TE8)

According to the general operating method described above, starting from 1,16-hexadecamethylene bis [4-methyl-5-(2-methoxyethyl) thiazolium] diiodide, T8, and using benzoyl chloride, a yellowish oil is obtained (Yield=72%).

NMR $^1$H (250 MHz, CDCl$_3$): δ 7.90–7.36 (m, 12H, CHO+ArH), 3.50–3.32 (m, 8H, CH$_3$OCH$_2$—, N—CH$_2$), 3.30 (s, 6H, CH$_3$O), 2.75 (t, 4H, CH$_3$CCH$_2$CH$_2$—), 2.06 (s, 6H, CH$_3$—C=), 1.57–1.09 (m, 28H, —(CH$_2$)$_{10}$—).

MS ES$^+$: m/e 781 ([M+H]$^+$, 100).

1.6 Synthesis of N,N'-diformyl-N,N'-di[1(2-oxo-4,5-dihydro-1,3-oxathian-4-ylidene)ethyl]1,12-diaminododecane (TE3)

2.8 mmoles (2 g) of thiazolium salt T3 [1,12-dodecamethylene bis [4-methyl-5-(2-hydroxyethyl) thiazolium dibromide] are dissolved in 4.4 mL of ethanol and 12.2 mmol (4.5 mL, 4 equivalents) of NaOH (10%) are added. The solution obtained is left under magnetic stirring for 15 min. Then, 6 mL (1.12 g, 2 equivalents) of 4-nitrophenylchloroformate in solution in ethyl acetate are added dropwise and the reaction mixture is stirred at ambient temperature for 2 hours. Ethyl acetate is added. The organic phase is washed successively with water, a saturated solution of sodium hydrogen carbonate, water, then dried over MgSO$_4$ and concentrated in an evaporator. The yellow oil obtained is purified over silica gel (eluent CH$_2$Cl$_2$, then adding 1% MeOH, then 2%). Yield: 20%.

NMR $^1$H (250 MHz, CDCl$_3$): δ 8.2 and 7.88 (2s, 2H, CHO); 4.43–4.40 (t, 4H, —CH$_2$OCO—); 3.33–3.27 (t, N—CH$_2$); 2.79–2.77 (t, 4H, CH$_2$—CH$_2$=); 1.88(s, 6H, CH$_3$; 1.46–1.13 (m, 20H, (CH$_2$)$_{10}$).

MS ES$^+$: m/e 541 ([M+H]$^+$, 100).

2. Synthesis of Thioesters of the C Duplicated Series

2.1. C5 Duplicated Compounds Comprising an O in the Alkyl Chain (TE9 and TE10):

These prodrugs are synthesized according to the general operating method described previously (Diagram 2).

Starting from 3,10-dioxadodecamethylenebis[5-(1,4-dimethyl)thiazolium] diiodide, T9, and p-methoxybenzoyl chloride, 2,17-(N,N'-diformyl-N,N'-dimethyl)diamino-3,16-S-thio-p-methoxybenzoyl-6,13-dioxaoctadeca-2,16-diene, TE9 is obtained, in the form of a colourless oil. Yield 65%.

NMR $^1$H (200 MHz, CDCl$_3$): δ 7.93–6.87 (m, 10H, CHO+ArH), 3.58 (s, 6H, 2CH$_3$), 3.55 (t, 4H, 2CH$_2$), 3.37 (t, 4H, 2CH$_2$), 2.89 (s, 6H, 2CH$_3$), 2.77 (t, 4H, 2CH$_2$), 2.03 (s, 6H, 2CH$_3$), 1.52–1.30 (m, 8H, 4CH$_2$).

Starting from 3,10-dioxadodecamethylenebis[5-(1-benzyl, 4-methyl)-thiazolium] dibromide, T10, and p-methoxybenzoyl chloride, 2,17-(N,N'-diformyl-N,N'-dibenzyl)diamino-3,16-S-thio-p-methoxybenzoyl-6,13-dioxaoctadeca-2,16-diene, TE10, is obtained in the form of a colourless oil. Yield: 70%.

NMR $^1$H (200 MHz, CDCl$_3$): δ 8.06–6.92 (m, 20H, CHO+ArH), 4.68 (s, 4H, 2CH$_2$), 3.91 (s, 6H, 2CH$_3$), 3.50 (t, 4H, 2CH$_2$), 3.38 (t, 4H, 2CH$_2$), 2.75 (t, 4H, 2CH$_2$), 2.07 (s, 6H, 2CH$_3$), 1.56–1.31 (m, 8H, 4CH$_2$).

TABLE 3

| compounds | R$_1$ | IC$_{50}$ (nM) |
|---|---|---|
| TE9 | CH$_3$ | 260 |
| TE10 | C$_6$H$_5$—CH$_2$ | 12 |

2.2. C5 Duplicated Compounds not Comprising O in the Alkyl Chain (TE12 and TE13):

These prodrugs are synthesized according to the general operating method described previously (Diagram 2).

Starting from dodecamethylenebis[5-(1-methyl-4-ethoxycarbonylethyl)-thiazolium] diiodide, T12, ethyl 3,18-(N,N'-diformyl-N,N'-dimethyl)diamino-4,17-S-thiobenzoyleicosa-3,17-dienedioate, TE12, is obtained. Colourless oil. Yield 70%.

NMR $^1$H (200 MHz, CDCl$_3$): δ 7.94–7.39 (m, 12H, CHO+ArH), 4.14 (q, 4H, 2OCH$_2$—), 3.45 (s, 4H, 2CH$_2$), 2.88 (s, 6H, 2CH$_3$), 2.44 (t, 4H, 2CH$_2$), 1.27–1.19 (m, 26H, —(CH$_2$)$_{10}$+2CH$_3$).

Starting from dodecamethylenebis[5-(1-benzyl-4-ethoxycarbonylethyl)-thiazolium] dibromide, T13, ethyl 3,18-(N,N'-diformyl-N,N'-dibenzyl)diamino-4,17-S-thiobenzoyleicosa-3,17-dienedioate, TE13, is obtained. Colourless oil. Yield 64%.

NMR $^1$H (200 MHz, CDCl$_3$): δ 8.24–7.26 (m, 22H, CHO+ArH), 4.70 (s, 4H, 2CH$_2$—Ar), 4.23 (q, 4H, 2OCH$_2$—), 3.44 (s, 4H, 2CH$_2$), 2.51 (t, 4H, 2CH$_2$), 1.52–1.29 (m, 26H, —(CH$_2$)$_{10}$+2CH$_3$).

TABLE 4

| compounds | R$_1$ | IC$_{50}$ (nM) |
|---|---|---|
| TE12 | CH$_3$— | 16 |
| TE13 | C$_6$H$_5$—CH$_2$— | 650 |

2.3. C4 Duplicated Compounds not Comprising O in the Alkyl Chain.

These prodrugs are synthesized according to the general operating method described previously (Diagram 2).

Starting from dodecamethylenebis[4-(1-methyl)-thiazolium]di-iodide, T15, 2,15-(N,N'-diformyl-N,N'-dimethyl)diamino-1,16-S-thiobenzoyl-hexadeca-1,15-diene, TE15, is obtained. Colourless oil. Yield 70%.

NMR $^1$H (200 MHz, CDCl$_3$): δ 7.94–7.39 (m, 12H, CHO+ArH), 5.7 (2H, =CH), 2.88 (s, 6H, 2N—CH$_3$), 2.48 (t, 4H, 2 =C—CH$_2$), 1.27–1.19 (m, 20H, —(CH$_2$)$_{10}$).

Starting from dodecamethylenebis[4-(1-benzyl)-thiazolium] dibromide, T16, 2,15-(N,N'-diformyl-N,N'-dibenzyl)diamino-1,16-S-thiobenzoyl-hexadeca-1,15-diene, TE16, is obtained. Colourless oil. Yield 64%.

NMR $^1$H (200 MHz, CDCl$_3$): δ 8.24–7.56 (m, 22H, CHO+ArH), 5.7 (2H, =CH), 4.37 (s, 4H, 2CH$_2$—Ar), 2.51 (t, 4H, 2 =C—CH$_2$), 1.52–1.29 (m, 20H).

TABLE 5

| compounds | R$_1$ | IC$_{50}$ (nM) |
|---|---|---|
| TE15 | CH$_3$— | 7 nM |
| TE16 | C$_6$H$_5$—CH$_2$— | 12 nM |

II. SYNTHESIS Of THIAZOLIUM SALTS

A. Synthesis of the Compounds of the N Duplicated Series (Compounds T3, T4, T6 and T8):

Diagram 3

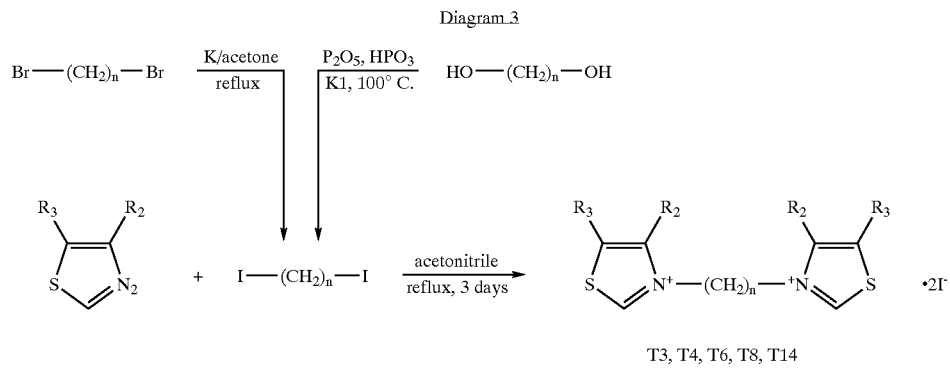

T3, T4, T6, T8, T14

General Operating Method for the Synthesis of Dihalides of α,ω-polymethylene bis Thiazolium:

Appropriately substituted thiazole (11.5 mmol) is dissolved in 30 mL of acetonitrile. 3.8 mmol of alkyl diiodide (or dibromide) are added and the reaction mixture is taken to reflux for 3 days. The solution is concentrated with a rotary evaporator and the oily residue obtained is taken up in water and ether. The aqueous phase is washed with ether then concentrated under reduced pressure. The product is then crystallized from isopropanol.

1,12-diiodododecane is synthesized as follows: 10.229 (1 equivalent) of 1,12-dibromododecane is mixed with 14.26 g (3 equivalents) of sodium iodide in 150 mL of acetone. After stirring for 15 minutes at ambient temperature, the solution is heated under reflux for 3 hours.

The acetone is then evaporated off with the rotary evaporator, the residue is taken up in ethyl ether and water and the product is extracted three times with ether. The ethereal phases are combined and are dried over magnesium sulphate. The white solid obtained is then recrystallized from methanol (M.p. 42–43° C.). Yield=95%. 1,16-diiodohexadecane is obtained from hexadecane-1,16-diol, by adding 5 g of this diol and 19 g of potassium iodide to a solution of 2.5 g of phosphoric anhydride and 5.2 mL of 85% phosphoric acid. The mixture is heated at 100° C. for 5 hours. A dense oil forms, and the mixture is poured into 50 mL of water. The organic phase is separated, and the aqueous phase extracted with ether. The organic phases are discoloured by stirring with 50 mL of a 10% solution of sodium thiosulphate. The ether is evaporated off. The oil obtained is crystallized from methanol (M.p.=52° C.). Yield: 82%.

1-Synthesis of 1,12-dodecamethylene bis [4-methyl-5-(2-hydroxyethyl)thiazolium] dibromide (T3)

According to the operating method described above, a hygroscopic white powder is obtained starting from 4-methyl-5-[2-hydroxyethyl] thiazole and 1,12-dibromododecane (Yield=75%)

NMR $^1$H (250 MHz, DMSO D$_6$): δ 10.08 (s, 2H, S—CH=), 4.45 (t, 4H, $^+$N—CH$_2$—), 3.62 (t, 4H, HOCH$_2$CH$_2$—), 3.02 (t, 4H, HOCH$_2$CH$_2$—), 2.50 (s, 6H, CH$_3$—C=), 1.77 (m, 4H, $^+$N—CH$_2$CH$_2$—), 1.60–1.25 (m, 16H, —(CH$_2$)$_8$—).

MS ES$^+$: m/e 227 (M$^{++}$, 100), m/e 533–535 (M$^{++}$Br$^-$, 10)

2-Synthesis of 1,12-decamethylene bis[4-methyl-5-(2-methoxyethyl)thiazolium] diiodide (T4)

According to the general operating method described above, a hygroscopic white powder is obtained starting from 4-methyl-5-(2-methoxyethyl) thiazole and 1,12-diiodododecane (Yield=70%)

NMR $^1$H (250 MHz, CDCl$_3$): δ 10.92 (s, 2H, S—CH=), 4.66 (t, 4H, $^+$N—CH$_2$—), 3.60 (t, 4H, CH$_3$OCH$_2$CH$_2$—), 3.35 (s, 6H, CH$_3$O), 3.07 (t, 4H, CH$_3$OCH$_2$CH$_2$—), 2.52 (s, 6H, CH$_3$—C=), 1.92 (m, 4H, $^+$N—CH$_2$CH$_2$—), 1.57–1.25 (m, 16H, —(CH$_2$)$_8$—).

MS ES$^+$: m/e 241 (M$^{++}$, 100), m/e 609 (M$^{++}$I$^-$, 5)

4-methyl-5-[2-methoxyethyl] thiazole is synthesized according to the process below:

10.20 mL of 4-methyl-5-[2-hydroxyethyl] thiazole is dissolved in 180 mL of anhydrous DMSO and 19 g of powdered potash are added. After stirring for 5 minutes, 5.30 mL of methyl iodide is introduced. The reaction mixture is stirred for 30 minutes at ambient temperature under an inert atmosphere. On completion of the reaction (monitored by TLC), the mixture is poured into 100 mL of water followed by extraction 3 times with ether. The organic phase is then washed with water, then with water saturated in NaCl and finally, dried over sodium sulphate. The product obtained is purified on silica gel eluting with an AcOEt/hexane mixture (1/3). A yellow oil is obtained (Yield=60%)

NMR $^1$H (250 MHz, CDCl$_3$): δ 2.39 (s, 3H, CH$_3$C=), 3.00 (t, 2H, —CH$_2$C=), 3.36 (s, 3H, CH$_3$O), 3.55 (t, 2H, O—CH$_2$—), 8.56 (s, 1H, S—CH=).

3-Synthesis of 1,12-dodecamethylenebis(4-methylthiazolium) diiodide (T6)

According to the general operating method described above, a white powder is obtained starting from 4-methylthiazole and 1,12-diiodododecane (Yield=50%)

NMR $^1$H (250 MHz, DMSO D6): δ 10.11 (s, 2H, S—CH=), 8.02 (s, 2H, S—CH=), 4.42 (t, 4H, $^+$N—CH$_2$—), 2.55 (s, 6H, CH$_3$—C=), 1.80 (m, 4H, $^+$N—CH$_2$CH$_2$—), 1.25 (m, 16H, —(CH$_2$)$_8$—).

MS ES$^+$: m/e 183 (M$^{++}$, 100), m/e 493 (M$^{++}$I$^-$, 5)

4-Synthesis of 1,16-hexadecamethylenebis[4-methyl-5-(2-methoxyethyl)thiazolium] diiodide (TB)

According to the general operating method described above, a white powder is obtained starting from 4-methyl-5-[2-methoxyethyl] thiazole and 1,16-diiodohexadecane (Yield=80%). M.p.: 210° C.

NMR $^1$H (250 MHz, CDCl$_3$): δ 10.92 (s, 2H, S—CH=), 4.66 (t, 4H, $^+$N—CH$_2$—), 3.60 (t, 4H, CH$_3$OCH$_2$CH$_2$—), 3.35 (s, 6H, CH$_3$O), 3.07 (t, 4H, CH$_3$OCH$_2$CH$_2$—), 2.52 (s, 6H, CH$_3$—C=), 1.92 (m, 4H, $^+$N—CH$_2$CH$_2$—), 1.57–1.25 (m, 24H, —(CH$_2$)$_8$—).

MS ES⁺: m/e 269 (M⁺⁺, 100), m/e 665 (M⁺⁺I⁻, 10)

TABLE 6

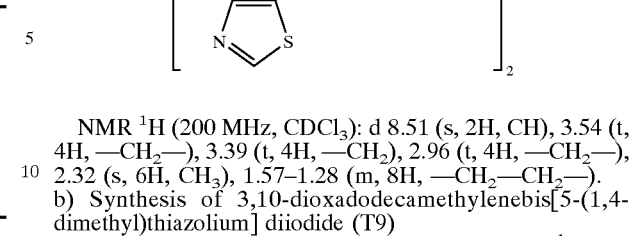

| compounds | R₃ | n | X | IC₅₀ (nM) |
|---|---|---|---|---|
| T3 | —CH₂—CH₂—OH | 12 | Br | 2.25 |
| T4 | —CH₂—CH₂—OCH₃ | " | " | 0.65 |
| T6 | H | " | I | 3 |
| T8 | —CH₂—CH₂—OCH₃ | 16 | " | 1.1 |

B. Synthesis of Compounds of the C Duplicated Series (T9, T10, T12 and T13):

1-Synthesis of the Compounds Duplicated on the C5 Carbon of the Thiazole Ring
1-1-Synthesis of the Compounds Comprizing an O in the Alkyl Chain (T9, T10):

Diagram 4

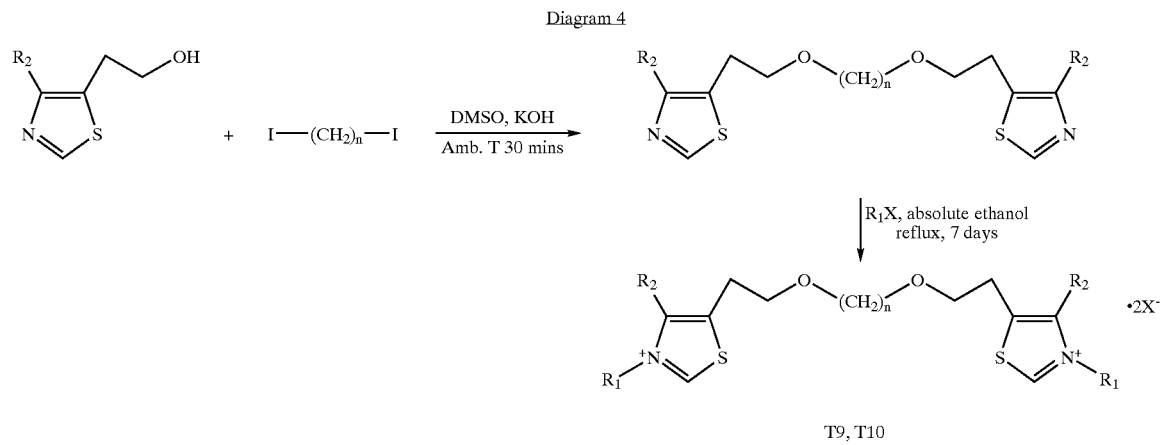

T9, T10

General Operating Method for the Synthesis of the Diiodides of 3,10-dioxadodecamethylenebis[5-(1-alkyl-4-methyl)thiazolium]: T9, T10) (Diagram 4).

1ˢᵗ stage: Dissolve 4-methyl-5-hydroxyethylthiazole (20.9 mmol) in anhydrous DMSO (50 ml). Add potassium hydroxide (83.6 mmol) and stir for 10 minutes. Add the diiodinated derivative (6.9 mmol) and stir at ambient temperature for 30 minutes. Add water and extract 3 times with ether. Wash the ethereal phase with water, then dry it over sodium sulphate. Purify by chromatography on silica gel eluting with AcOEt-Hexane (1-3).

2ⁿᵈ stage: Alkylation of bis-thiazole: Dissolve bis-thiazole (1 mmol) in absolute ethanol (40 ml). Add the desired halogenated derivative (2 mmol) and heat the mixture under reflux for approximately one week. Evaporate the ethanol and recrystallise from an iPrOH-(iPr)₂O mixture.

a) Synthesis of 1,6-bis[2-(4-methylthiazol-5-yl)ethoxyhexane:

According to the general operating method (1ˢᵗ stage) described above, a colourless oil is obtained starting from 4-methyl-5-hydroxyethylthiazole and 1,6-diiodohexane (Yield=60%)

NMR ¹H (200 MHz, CDCl₃): d 8.51 (s, 2H, CH), 3.54 (t, 4H, —CH₂—), 3.39 (t, 4H, —CH₂), 2.96 (t, 4H, —CH₂—), 2.32 (s, 6H, CH₃), 1.57–1.28 (m, 8H, —CH₂—CH₂—).

b) Synthesis of 3,10-dioxadodecamethylenebis[5-(1,4-dimethyl)thiazolium] diiodide (T9)

According to the general operating method (2ⁿᵈ stage) described above, a hygroscopic white solid is obtained starting from the product previously obtained and methyl iodide (Yield=60%)

NMR ¹H (200 MHz, CDCl₃): d 10.99 (s, 2H, S—CH=), 4.33 (s, 6H, 2N⁺CH₃), 3.71 (t, 4H, 2CH₂—O), 3.52 (t, 4H, 2O—CH₂), 3.03 (t, 4H, 2CH₂), 2.51 (s, 6H, 2 =C—CH₃), 1.65–1.47 (m, 8H, 4-CH₂—).

c) Synthesis of 3,10-dioxadodecamethylenebis[5-(1-benzyl, 4-methyl)-thiazolium] dibromide (T10)

According to the general operating method (2ⁿᵈ stage) described above, a hygroscopic white solid is obtained starting from the product obtained in the 1ˢᵗ stage and benzyl bromide (Yield=74%)

NMR ¹H (200 MHz, CDCl₃): d 11.45 (s, 2H, S—CH=), 7.36–7.28 (m, 10H, 2ArH), 3.65 (t, 4H, 2CH₂—O), 3.44 (t, 4H, 2O—CH₂), 3.03 (t, 4H, 2CH₂), 2.51 (s, 6H, 2 =C—CH₃), 1.57–1.34 (m, 8H, 4-CH₂—).

TABLE 7

| compounds | R₁ | X | IC₅₀ (nM) |
|---|---|---|---|
| T9 | CH₃— | I | 70 |
| T10 | C₆H₅—CH₂— | Br | 2.5 |

1-2-Compounds not Comprizing an O in the Alkyl Chain (T12, T13)

This synthesis is carried out in 4 stages according to Diagram 5.

Diagram 5

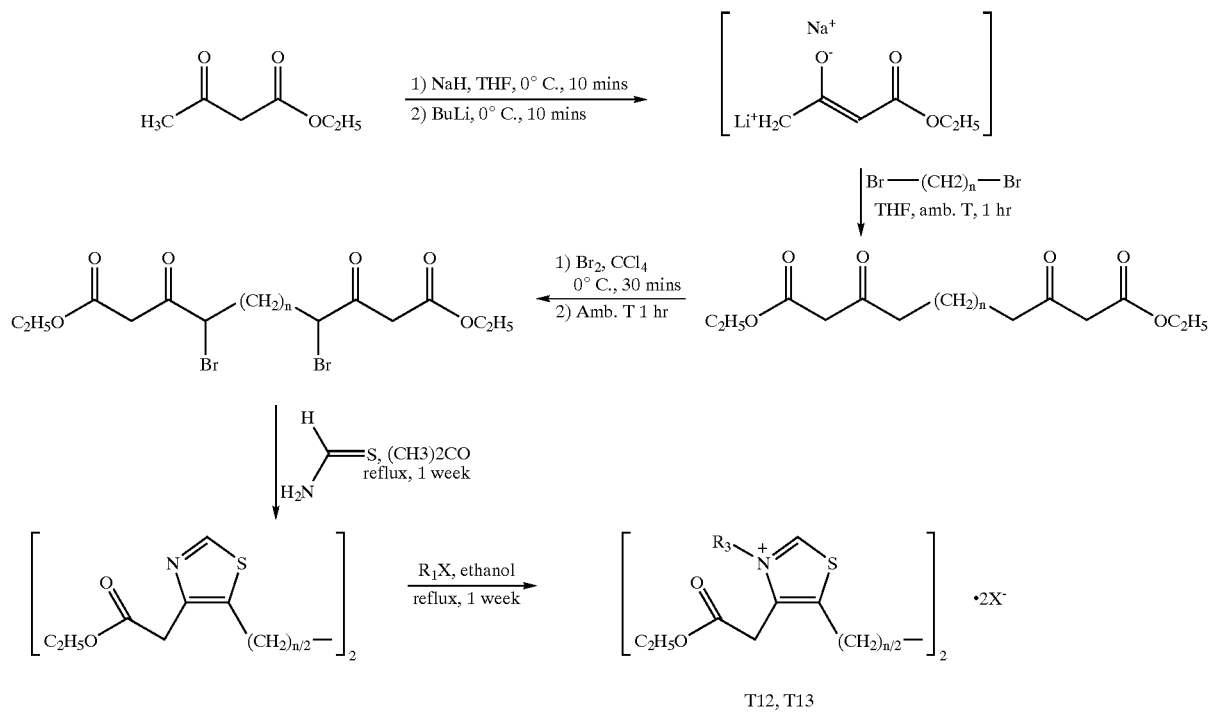

T12, T13 a) Synthesis of Ethyl 3,18-dioxoeicosanedioate:

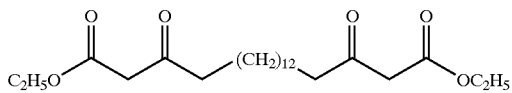

In a two-necked flask under argon, NaH (43.7 mmol) is put into suspension in anhydrous THF (100 ml). The reaction medium is cooled down in an ice bath and acetoethyl acetate is added dropwise (39.7 mmol). After stirring for 10 minutes at 0° C. n-BuLi is added dropwise (1.56 M; 43.7 mmol). Stirring is carried out for a further 10 minutes at ambient temperature before proceeding with alkylation.

Dibromododecane (15.9 mmol) in solution in 20 ml of anhydrous THF is added dropwise to the previous solution. The reaction medium is allowed to return to ambient temperature and stirring is continued for 1 hour. Water is added followed by extraction with ether (3 times). The organic phase is washed with a saturated NaCl solution, dried over sodium sulphate, filtered and evaporated to dryness. The product is purified by chromatography on silica-gel eluting with AcOEt-Hexane (1-1). A white solid is obtained (Yield=65%); M.p.=60° C.

NMR $^1$H (200 MHz, CDCl$_3$): d 4.16 (q, 4H, 2CH$_2$), 3.41 (s, 4H, 2CH$_2$), 2.50 (t, 4H, 2CH$_2$), 1.56–121 (m, 30H).

b) Synthesis of Ethyl 4,17-dibromo-3,18-dioxoeicosanedioate:

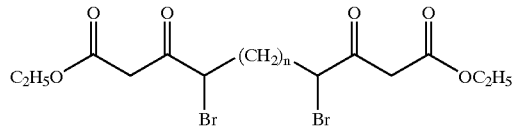

The previous compound (3.8 mmol) is dissolved in 20 ml of CCl$_4$. The solution is cooled down to 0° C., and bromine is added dropwise (76 mmol), stirring is maintained at the same temperature for 30 minutes, then at ambient temperature for 1 hour. The solvent is evaporated off. The residue is dissolved in water, followed by extraction with ethyl acetate. The organic phase is dried over sodium sulphate, filtered and evaporated to dryness. Chromatography is carried out on silica gel eluting with AcOEt-Hexane (1-1). A yellowish oil is obtained (Yield=64%).

NMR $^1$H (200 MHz, CDCl$_3$): d 4.42 (m, 6H, 2CH$_2$+CH), 3.78–3.48 (m, 4H, 2CH$_2$), 1.94–1.14 (m, 30H).

c) Synthesis of dodecamethylenebis[5-(4-ethoxycarbonylethyl)thiazole]:

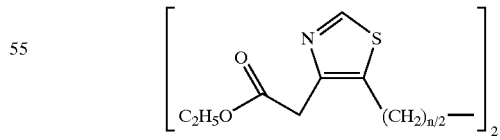

Thioformamide (23.4 mmol) in solution in 5 ml of acetone is added to a solution of 11.7 mmol of ethyl bis-bromoacetoacetate in 5 ml of acetone and the reaction medium is stirred at 40° C. for one week. The solvent is evaporated off and the residue is dissolved in water. The solution is extracted with AcOEt. Purification is carried out by chromatography (AcOEt-Hex: 1/1). A white solid is obtained (Yield=50%); M.p.=112–114° C.

NMR $^1$H (200 MHz, CDCl$_3$): d 8.54 (s, 2H, 2CH), 4.17 (q, 4H, 2CH$_2$), 3.72 (s, 4H, 2CH$_2$), 2.72 (t, 4H, 2CH$_2$), 1.56–121 (m, 30H)

d) Alkylation of dodecamethylenebis[5-(4-ethoxycarbonyl ethyl)thiazole]:

The previous compound leads by alkylation on the nitrogen atom (according to the usual process described for T3 or T4) either to T12 using iodomethane, or to T13 using benzyl bromide.

Dodecamethylenebis[5-(1-methyl-4-ethoxycarbonylethyl)-thiazolium) diiodide (T12):

Yellow solid M.p.=112° C.; Yield=55%

NMR $^1$H (200 MHz, CDCl$_3$): d 10.91 (d, 2H, 2CH), 4.42 (6H, N—CH$_3$), 4.25–4.16 (m, 8H, 2CH$_2$+2CH$_2$), 2.91 (m, 4H, 2CH$_2$), 1.62–1.26 (m, 26H).

Dodecamethylenebis[5-(1-methyl-4-ethoxycarbonylethyl)-thiazolium] dibromide (T13):

Yellow oil; Yield=50%

NMR $^1$H (200 MHz, CDCl$_3$): d 11.26 (d, 2H, 2CH), 7.36–7.26 (m, 10H, ArH), 6.07 (s, 4H, 2CH$_2$), 4.02–3.92 (m, 12H, 6CH$_2$), 2.91 (m, 4H, 2CH$_2$), 1.62–1.26 (m, 26H).

TABLE 8

| compounds | R$_1$ | X | IC$_{50}$ (nM) |
|---|---|---|---|
| T12 | CH$_3$— | I | 13 |
| T13 | C$_6$H$_5$—CH$_2$— | Br | 250 |

2-Synthesis of Compounds Duplicated on the C4 Carbon of the Thiazole Ring (T15 and T16)

This synthesis is carried out in 5 stages according to Diagram 6.

Tetradecanedioic acid is converted into its chloride (Jayasuriya et al.; J. Amer. Chem. Soc.; 112; 15; 1990; 5844–5850). The latter is treated with diazomethane in is order to produce 1,16-bis-diazo-hexadecane-2,15-dione (Canonica et al.; Atti Accad. Naz. Lincei Cl. Sci. Fis. Mat. Nat. Rend.; 8.10; 1951; 479–484), which is treated with HCl and produces 1,16-dichlorohexadecane-2,15-dione (same reference). This compound is then treated with thioformamide under the same conditions as for the synthesis of dodecamethylenebis[5-(4-ethoxycarbonylethyl) thiazole] (Diagram 5, 3$^{rd}$ stage) in order to produce dodecamethylenebis(4-thiazole).

This leads by alkylation on the nitrogen atom (according to the usual process described for T3 or T4) either to dodecamethylenebis[4-(1-methyl)-thiazolium] diiodide, T15, using iodomethane, or to dodecamethylenebis[4-(1-benzyl)-thiazolium] dibromide, T16, using benzyl bromide.

TABLE 9

| compounds | R$_1$ | X | IC$_{50}$ (nM) |
|---|---|---|---|
| T15 | CH$_3$— | I | 4 |
| T16 | C$_6$H$_5$—CH$_2$— | Br | 10 |

III. SYNTHESIS OF HALOALKYLAMINES

1) N,N'-dimethyl-N,N'-(5-chloropentyl)-1,16-hexadecane diamine hydrochloride (P1).

a) 5-methylamino-1-pentanol.

10.8 g (0.088 mole) of 5-chloro-1-pentanol is added to 45 ml of an 8M solution of MeNH$_2$ (0.36 mole) in MeOH. The reaction mixture is heated to 100° C. in an autoclave for 48 hours. The residue obtained after evaporation of the MeOH is distilled under reduced pressure in order to produce 6.2 g (65%) of aminoalcohol.

NMR $^1$H (CDCl$_3$) δ 3.60 (t, 2H, CH$_2$OH), 2.56 (t, 2H, CH$_2$NH), 2.40 (s, 3H, CH$_3$NH), 2.66–1.32 (m, 6H, (CH$_2$)$_3$).

MS (Electrospray, positive mode) m/z 118 (M+H)$^+$, 100).

b) N,N'-dimethyl-N,N'-(5-hydroxypentyl)-1,16-hexadecanediamine.

0.57 g (0.0048 mole) of diisopropylethylamine and 0.58 g (0.0045 mole) of 5-methylamino-1-pentanol are added to 1.08 g (0.0022 mole) of diiodohexadecane dissolved in 50 mL of ethanol. The reaction mixture is heated under reflux for 48 hours, the ethanol is then eliminated under reduced pressure. TLC analysis of the residue shows the formation of the expected product and indicates the presence of a small quantity of a very polar compound identified by mass spectrometry as being the quaternary ammonium salt shown in the figure below.

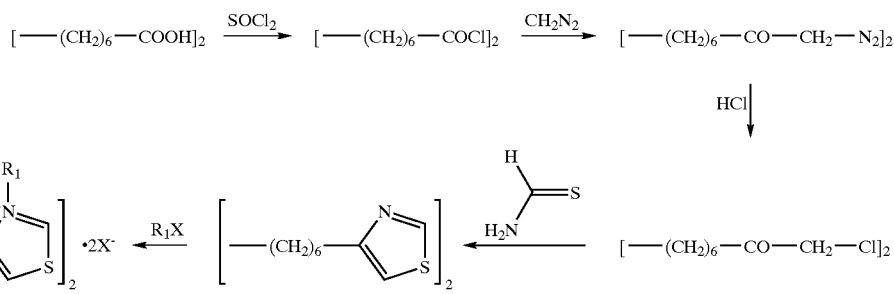

Diagram 6

T15, T18

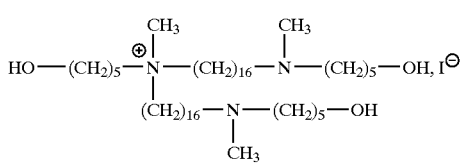

The residue is partially dissolved in water and N,N'-dimethyl-N,N'-(5-hydroxypentyl)-1,16-hexadecanediamine is extracted in ether with $K_2CO_3$, leaving the polar contaminant in the water. The ethereal phases are dried over $MgSO_4$, filtered and concentrated under reduced pressure.

NMR $^1H$ (CDCl$_3$) δ 3.60 (t, 4H, CH$_2$OH), 2.65–2.40 (m, 8H, CH$_2$—NH—CH$_2$), ), 2.37 (s, 6H, CH$_3$N), 1.60–1.21 (m, 40H, 2(CH$_2$)$_3$+(CH$_2$)$_{14}$).

c) N,N'-dimethyl-N,N'-(5-chloropentyl)-1,16-hexadecanediamine hydrochloride (P1).

The residue obtained above is dissolved in 10 ml of $CH_2Cl_2$ and 1.7 ml of thionyl chloride is added. The reaction mixture is heated under reflux for 5 hours after which all the volatile products are eliminated under reduced pressure. The residue is triturated in ether until a precipitate appears. The precipitate is filtered then recrystallized from an ethanol-ether mixture in order to produce 0.408 g (32%) of N,N'-dimethyl-N,N'-(5-chloropentyl)-1,16-hexadecanediamine hydrochloride.

NMR $^1H$ (CDCl$_3$) δ 3.48 (t, 4H, CH$_2$Cl), 3.00–2.80 (m, 8H, CH$_2$—NH$^+$(CH$_3$)—CH$_2$)), 2.70 (d, 6H, CH$_3$NH$^+$), 1.86–1.19 (m, 40H, 2(CH$_2$)$_3$+(CH$_2$)$_{14}$).

MS (Electrospray, positive mode) m/z 247 (M$^{++}$, 100), m/z 529/531 (M$^{++}$Cl$^-$, 20).

2) N,N'-dimethyl-N,N'-(4-chloropentyl)-1,16-hexadecanediamine hydrochloride (P2)

a) 5-methylamino-2-pentanol.

10.59 g (0.10 mole) of γ-valerolactone is added to 10 60 ml of an 8M solution of MeNH$_2$ (0.48 mole) in MeOH.

The reaction mixture is heated at 100° C. in an autoclave for 48 hours. The residue obtained after evaporation of the excess MeNH$_2$ under reduced pressure is dissolved in 20 ml of THF and is added to a solution of 6.26 g (0.17 mol) of LiAlH$_4$ in 80 ml of THF for 1 hour in order to obtain a slight reflux. Reflux is maintained for 48 hours, a 5M soda solution is then added dropwise until a whitish suspension is obtained. The reaction mixture is extracted with ether, the ethereal phases are dried over anhydrous MgSO$_4$ and the solvent is eliminated under reduced pressure. The residue obtained is distilled under reduced pressure in order to produce 6.27 g (63%) of 5-methylamino-2-pentanol.

NMR $^1H$ (CDCl$_3$) δ 3.72 (m, 1H, CHOH), 2.76–2.48 (m, 2H, CH$_2$NH), 2.47 (s, 3H, CH$_3$NH), 2.66–1.32 (m, 6H, (CH$_2$)$_3$).

MS (Electrospray, positive mode) m/z 118 (M+H)$^+$, 100).

b) N,N'-dimethyl-N,N'-(4-hydroxypentyl)-1,16-hexadecanediamine.

0.59 g (4.6 mmole) of diisopropylethylamine and 0.61 g (5.8 mmole) of 5-methylamino-2-pentanol are added to 1.10 g (2.3 mmole) of diiodohexadecane dissolved in 50 mL of ethanol. The reaction mixture is taken to reflux for 48 hours, the ethanol is then eliminated under reduced pressure. TLC analysis of the residue shows the formation of the expected product and indicates the presence of a small quantity of a very polar compound identified by mass spectrometry as being the quaternary ammonium salt shown in the figure below

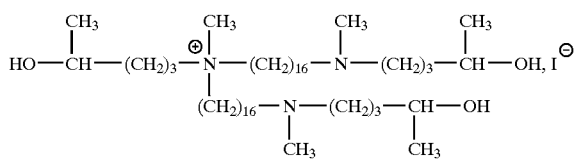

The residue is partially dissolved in water and N,N'-dimethyl-N,N'-(4-hydroxypentyl)-1,16-hexadecanediamine is extracted in ether with $K_2CO_3$, leaving the polar contaminant in the water. The ethereal phases are dried over MgSO$_4$, filtered and concentrated under reduced pressure.

NMR$^1H$ (CDCl$_3$) δ 3.70–3.58 (m, 2H, CHOH), 2.40–2.24 (m, 8H, CH$_2$—NH$^+$(CH$_3$)—CH$_2$), 2.16 (s, 6H, CH$_3$NH$^+$), 1.66–1.10 (m, 42H, 2(CH$_2$)$_2$+2(CH$_3$CH)+(CH$_2$)$_{14}$).

c) N,N'-dimethyl-N,N'-(4-chloropentyl)-1,16-hexadecanediamine hydrochloride (P2).

The residue obtained above is dissolved in 10 ml of $CH_2Cl_2$ and 2 mL of thionyl chloride is added. The reaction mixture is heated under reflux for 5 hours after which all the volatile products are eliminated under reduced pressure. The residue is triturated in ether until a precipitate appears. The precipitate is filtered then recrystallized from an ethanol-ether mixture in order to produce 0.415 g (32%) of N,N'-dimethyl-N,N'-(4-chloropentyl)-1,16-hexadecanediamine hydrochloride.

NMR $^1H$ (CDCl$_3$) δ 4.00 (m, 2H, CHCl), 3.00–2.87 (m, 8H, CH$_2$—NH$^+$(CH$_3$)—CH$_2$), ), 2.72 (d, 6H, CH$_3$NH$^+$), 1.86–1.19 (m, 42H, 2(CH$_2$)$_2$+2(CH$_3$CH)+(CH$_2$)$_{14}$).

MS (Electrospray, positive mode) m/z 247 (M$^{++}$, 100), m/z 529/531 (M$^{++}$Cl$^-$, 20).

Study of the Pharmacological Properties of Precursors According to the Invention A. Antimalarial Activity Against *P. falciparum* in vitro The results of the IC$_{50}$ values in nM for the prodrugs of disulphide type (Table 10) and those of thioester type (Table 11) according to the invention, as well as for the corresponding drugs, are presented in Tables 10 and 11 hereafter.

The IC$_{50}$ measurements are determined vis-à-vis *P. falciparum* according to the Desjardins method in which the incorporation of [$^3$H] hypoxanthine (FIG. 1) into the nucleic acids is an indicator of cell viability. In each case, optical microscopy controls are carried out.

TABLE 10

| TS prodrug (Ra = S—R) | | | | | T drug | |
|---|---|---|---|---|---|---|
| R | Z | R$_3$ | name | IC$_{50}$ (nM) | name | IC$_{50}$ (nM) |
| THF—CH$_2$— | —(CH$_2$)$_{12}$— | HO—CH$_2$—CH$_2$— | TS3a | 1 | T3 | 2.25 |
| C$_3$H$_7$— | | | TS3b | 1.3 | | |
| C$_6$H$_5$—CH$_2$— | — | | TS3c | 1.6 | | |
| HO—CH$_2$—CH$_2$— | | | TS3d | 2.5 | | |

TABLE 10-continued

| | | | | | | |
|---|---|---|---|---|---|---|
| $C_3H_7-$ | " | $CH_3O-CH_2-CH_2-$ | TS4b | 3.5 | T4 | 0.65 |
| $Et_2N(CH_2)_2-$ | | | TS4c | 2.8 | | |
| $C_3H_7-$ | " | $C_6H_5-COO-(CH_2)_2-$ | TS5 | 22 | / | |
| $C_3H_7-$ | " | H— | TS6b | 3.1 | T6 | 3 |

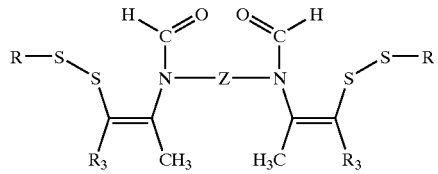

TABLE 11

A

| N-duplicated TE prodrugs ($R_a$ = RCO) | | | | T drug | |
|---|---|---|---|---|---|
| R | Z | name | $IC_{50}$ (nM) | name | $IC_{50}$ (nM) |
| $CH_3-$ | $-(CH_2)_{12}-$ | TE4a | 14 | T4 | 0.65 |
| $(CH_3)_3C-$ | " | TE4b | 12 | | |
| $C_6H_5-$ | " | TE4c | 2 | | |
| $p-CH_3O-C_6H_4-$ | " | TE4d | 3.4 | | |
| O\N—(CH_2)_2—O—C_6H_4— | " | TE4e | 6.4 | | |
| $(CH_2H_5)_2N-CH_2-C_6H_4-$ | " | TE4f | 2.3 | | |
| O\N—CH_2—C_6H_4— | " | TE4g | 2.3 | | |
| $CH_3OOC-C_6H_4-$ | " | TE4j | 2.7 | | |
| $C_6H_5-$ | $-(CH_2)_{16}$ | TE8 | 0.6 | T8 | 1.1 |
| [cyclic structure] | | TE3 | 2.6 | T3 | 2.25 |

B

| C-duplicated TE prodrugs ($R_a$ = RCO) | | | | | | T drug | |
|---|---|---|---|---|---|---|---|
| R | $R_1$ | $R_2$ | Z | name | $IC_{50}$ (nM) | name | $IC_{50}$ (nM) |
| $p-CH_3O-C_6H_4-$ | $C_6H_5-CH_2$ | $CH_3-$ | $-(CH_2)_2O(CH_2)_6O(CH_2)_2-$ | TE10 | 12 | T10 | 2.5 |
| $C_6H_5-$ | $CH_3-$ | $CH_2CO_2Et$ | $-(CH_2)_{12}-$ | TE12 | 16 | T12 | 13 |

TABLE 11-continued

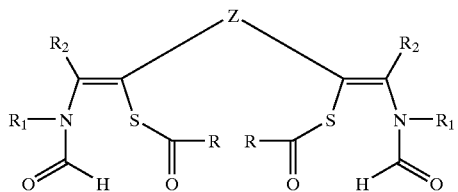

These results show that the $IC_{50}$ values obtained are very low both in the disulphide series and in the thioester series and are of the order of 1 to 14 nM for bis type derivatives with a spacer arm formed by a dodecyl chain.

It can be noted with interest that the $IC_{50}$ value for the ionized cyclized compounds is substantially of the same order of magnitude as that of the corresponding neutral prodrugs.

By way of comparison, the $IC_{50}$ value was measured on a compound which could not be cyclized by enzymatic hydrolysis and corresponding to the formula

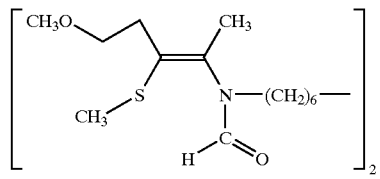

An $IC_{50}>10^{-5}$ M value which indicates that cyclization is necessary for strong antimalarial activity and also suggests that cyclization is effectively produced in the presence of serum and/or erythrocytes infected during the 48 hours of the in vitro test measuring antimalarial activity.

In Table 12 hereafter, the results of the $IC_{50}$ measurements carried out on haloalkylamines according to the invention are given. These results relate to the prodrugs called P1 and P2 and the corresponding cyclized derivatives G26 and G27 respectively.

TABLE 12

| Name | Z | $R'_1$ | $R_1$ | n | W | $IC_{50}$ (nM) |
|------|---|--------|-------|---|---|----------------|
| P1   | —(CH$_2$)16— | H | CH$_3$ | 4 | Cl | 1.7 |
| G26  | " | " | " | " | I | 0.55 |
| P2   | " | CH$_3$ | " | 3 | Cl | 0.5 |
| G27  | " | " | " | " | I | 1.4 |

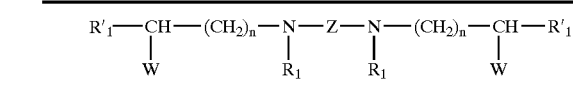

P1, P2

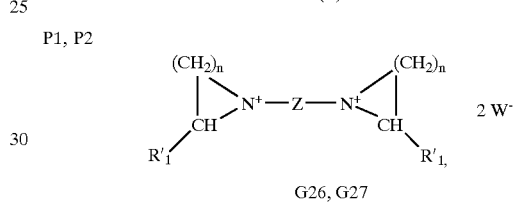

G26, G27

B) Antimalarial Activity in vivo Against a Mouse Infected by *P. vinckei* and Tolerance After Administration in Acute or Semi-chronic Conditions.

Table 13 hereafter shows the results obtained with prodrugs according to the invention of disulphide type (TS3b), of thioester type (TE4c, TE4a and TE4e), the corresponding drug T3 and, by way of comparison, the quaternary ammonium derivative G25.

TABLE 13

| Drug | In vitro $IC_{50}$ (nM) (*P. flaciparum*) | In vivo $LD_{50}$ (mg/kg) (mouse) acute[a] | semi-chronic[b] | Oral absorption index[c] | In vivo $ED_{50}$ (mg/kg) [TI] (*P. vinckei*) |
|------|---|---|---|---|---|
| G25 | 0.6 | ip 1.27<br>po 130 | 1.15<br>65 | 87 | 0.22 [5.2]<br>~15 [4.4] |
| T3 | 2.25 | ip 10<br>po 700 | 7.5<br>160 | 70 | n.d. |
| TS3b | 1.3 | ip 240<br>po 1600 | 90 (32*)<br>410 | 6.7 | ~7 [4.6* < TI ≦ 12.8]<br>~180 [2.3] |
| TE4c | 2 | ip 100<br>po ~1000 | ≧30[d]<br>~300 | ~10 | 1 [≧30][e]<br>30 > x > 1 [10 < TI < 100][e] |
| TE4a | 14 | ip ~50<br>po ~1000 | n.d. | ~20 | |
| TE4e | 6.4 | ip ~50 | | | |

The $IC_{50}$ is the concentration which inhibits by 50% the in vitro growth of *P. falciparum*; the $LD_{50}$ is the lethal dose corresponding to the death of 50% of the mice and the $ED_{50}$ is the effective dose for inhibiting by 50% the in vivo growth of *P. vinckei* according to a 4-day suppressive test, TI corresponds to the therapeutic index, TI=$LD_{50}$ (semi-chronic)/$ED_{50}$; ip: intraperitoneal administration; po: per os.

In this table, a) to e) have the following meanings:

a) corresponds to a single dose;

b) corresponds to administration twice per day, for 4 consecutive days;
c) corresponds to the $LD_{50}$ po/$LD_{50}$ ip ratio under acute administration conditions, which ratio is hereafter referred to as "oral absorption index";
d) corresponds to the death of only 25% of the mice.
"*" The $LD_{50}$ (semi-chronic) decreases in mice infected with malaria;
e) TE4c was used in a 50/50 mixture of PEG/castor oil.

These results show that the prodrugs of the invention have a strong antimalarial activity in vitro and in vivo as well as good tolerance and high absorption.

C) Pharmacokinetic Characteristics and Serum Level.

C1. Pharmacokinetic Parameters in the Mouse

The results of the pharmacokinetic parameters after administration by intraperitoneal or oral route in a mouse for a prodrug of disulphice type (TS3b) and a prodrug of thioester type (TE4c) are presented hereafter.

For determination of the serum level, bio-tests are used ex vivo: briefly, the medicament is administered to the animal, then repeated blood samples are taken. The sera are decomplemented for 30 minutes at 56° C. The active metabolite content is then determined by incubation of different concentrations (dichotomic dilution) of each serum, in the presence of suspensions of erythrocytes infected by P. falciparum, according to the DESJARDINS method with [$^3$H] hypoxanthine.

The results are expressed in $IS_{50}$, which corresponds to the percentage of serum (containing an active metabolite) capable of inhibiting the growth of P. falciparum by 50%.

This value is then converted into a serum concentration, (usually expressed in ng/ml) by testing the active compound directly (without passing through the animal), on the same suspension infected by P. falciparum and by determining its $IC_{50}$ value (in ng/ml) [serum level=$IC_{50}$] (in ng/ml)×100/ $IS_{50}$ (in %)].

The results are expressed as the log (serum level of medicaments), as a function of time, which allows the evaluation of the half-time for distribution to the serum compartment $t_{1/2(d)}$; the half-time for elimination of the serum compartment ($t_{1/2(e)}$); of $C_0$), corresponding to the serum level originally extrapolated during the elimination phase; the AUC (which indicates the quantity of drug circulating in the blood stream); and the relative bioavailability in the oral route administration method, as against the intraperitoneal route method [AUC (po)/AUC (ip)] which is an indicator of the degree of absorption by oral route.

Pharmacokinetics of TE4c

Doses of 3 and 50 mg per kg of TE4c are administered to mice by intraperitoneal route and by oral route, which corresponds to $LD_{50}/33$ and $LD_{50}/20$ respectively.

The compound is solubilized in 10% DMSO. Even at these low doses, high serum levels are observed with a diphasic pharmacokinetic profile for both routes. The results are given in FIG. 2 which indicates the concentration of seral active metabolite in ng/ml as a function of the time in hours.

In this figure, (-v-) corresponds to ip administration at 3 mg/kg and the curve with (-o-) corresponds to administration po at 50 mg/kg.

In the first phase, a peak is very rapidly observed (in less than two hours) with serum levels which decrease until 4 to 7 hours, then increase and a peak is again observed at around 15 hours, for both administration routes.

These results suggest a rapid first phase during which the prodrug is distributed and enters the serum compartment. Once in this compartment, the prodrug probably converts to a quaternary ammonium compound.

The second phase can then be carried out in order to determine the pharmacokinetic parameters of the ionized derivative.

Figure 2:
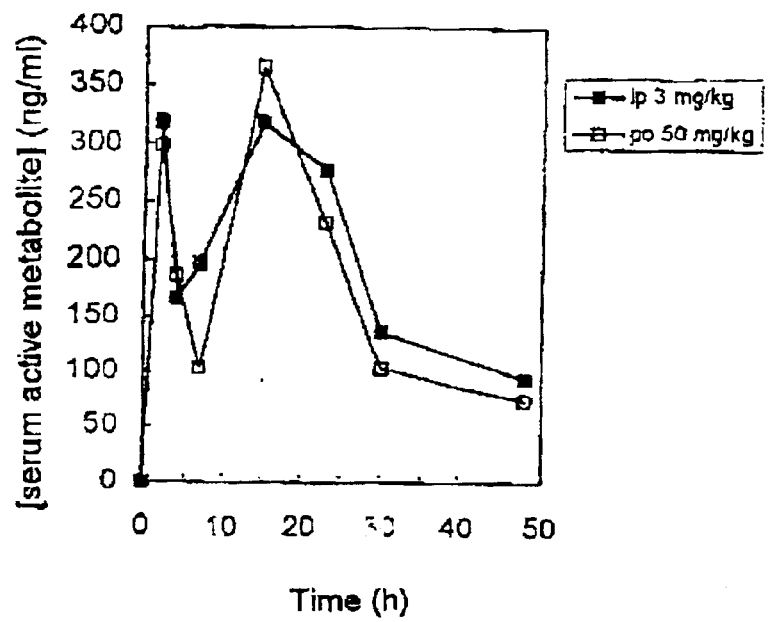
Figure 3:
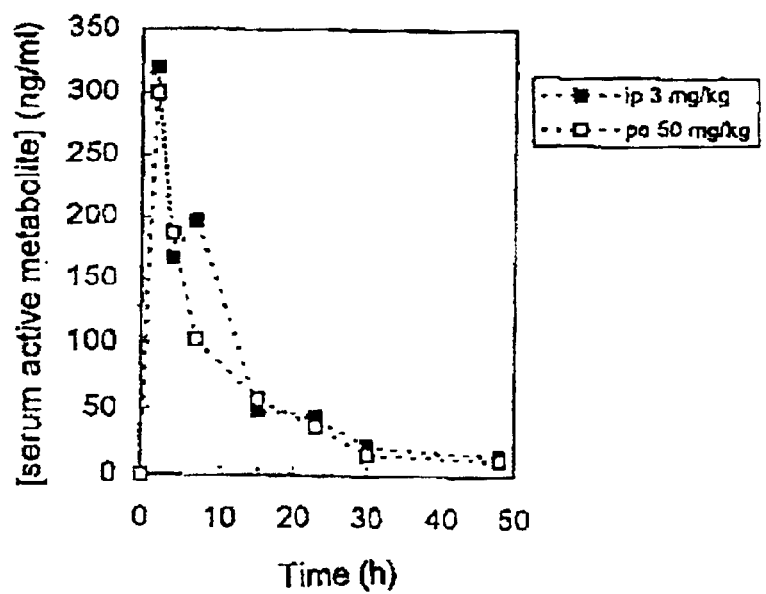
Figure 4:
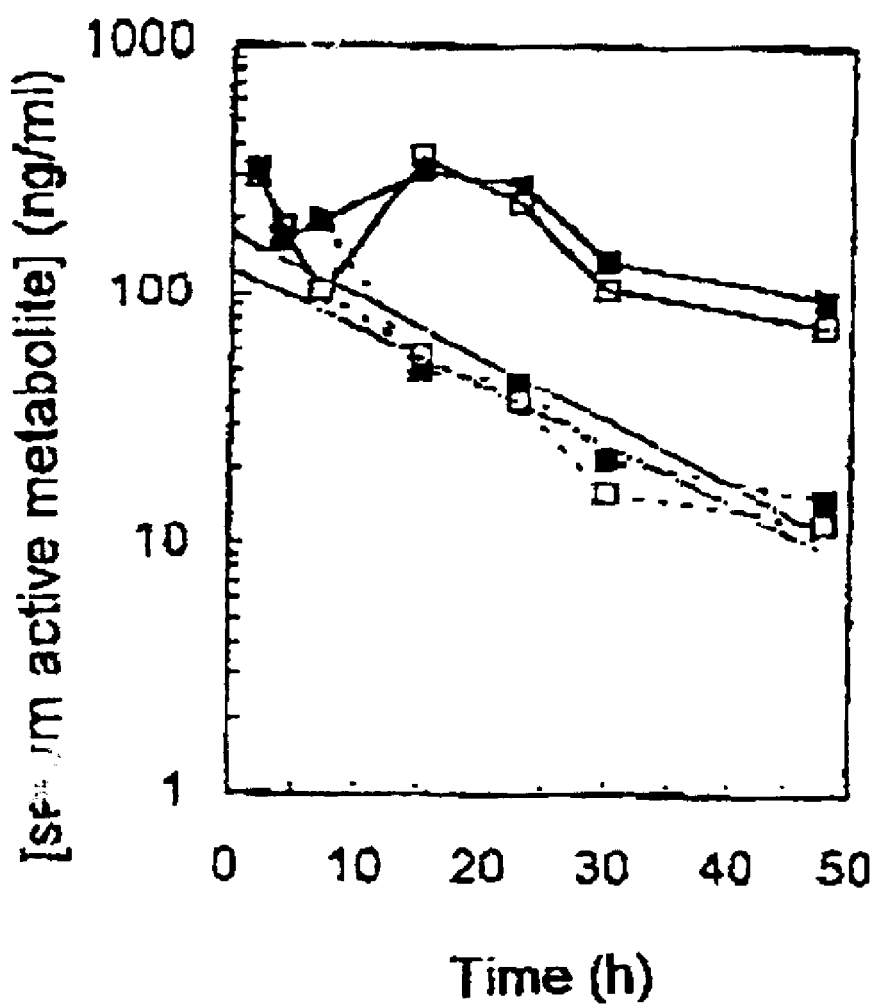

If the conversion to an ionized drug is considered to be total, the pharmacokinetic profile can be redrawn on the basis of the $IC_{50}$ of the drug and not on that of the prodrug (see FIG. 3, where the legends of the curves are the same as in FIG. 2). The semi-logarithmic representation allows the determination of the main pharmacokinetic parameters of the active metabolite (which is considered to be the quaternary ammonium drug T4) for both administration routes (see FIG. 4 where the results are redrawn from FIGS. 2 and 3). The pharmacokinetic parameters are $C_0$=180 ng/ml, $t_{1/2}$=12 hours, AUC=3.3 µg.hr/mL after ip administration at 3 mg/kg, and $C_0$=130 ng/ml, $t_{1/2}$=12 hours 30 minutes, AUC= 2.7 µg.h/ml after oral administration at 50 mg/kg. Under these conditions, the relative bioavailability is 5%.

In another series of experiments, the pharmacokinetics were studied at higher doses of TE4c (10 mg/kg ip and 150 mg/kg po).

Figure 5A:
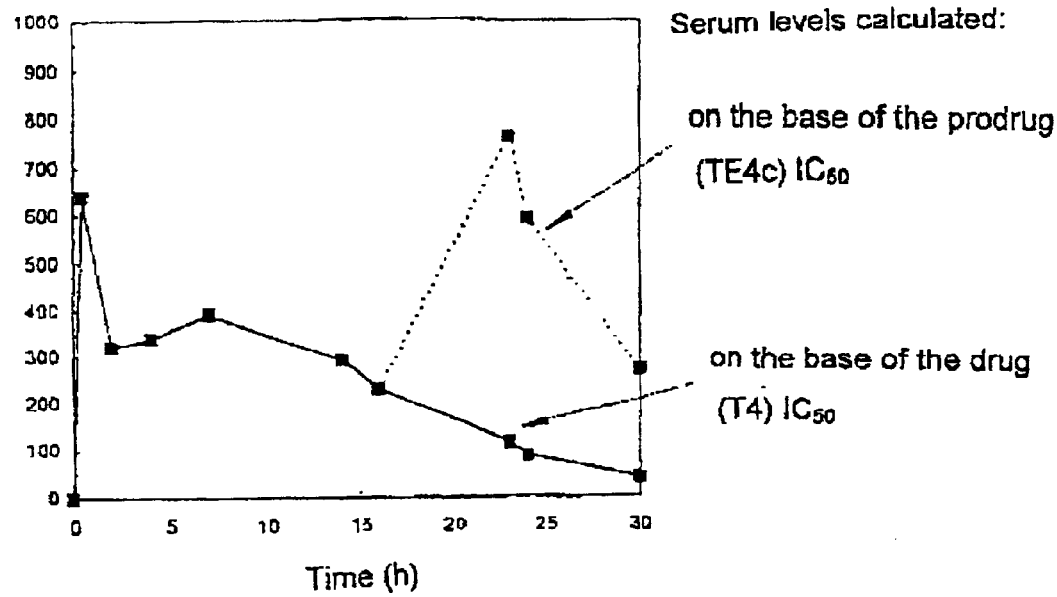
Figure 5B:
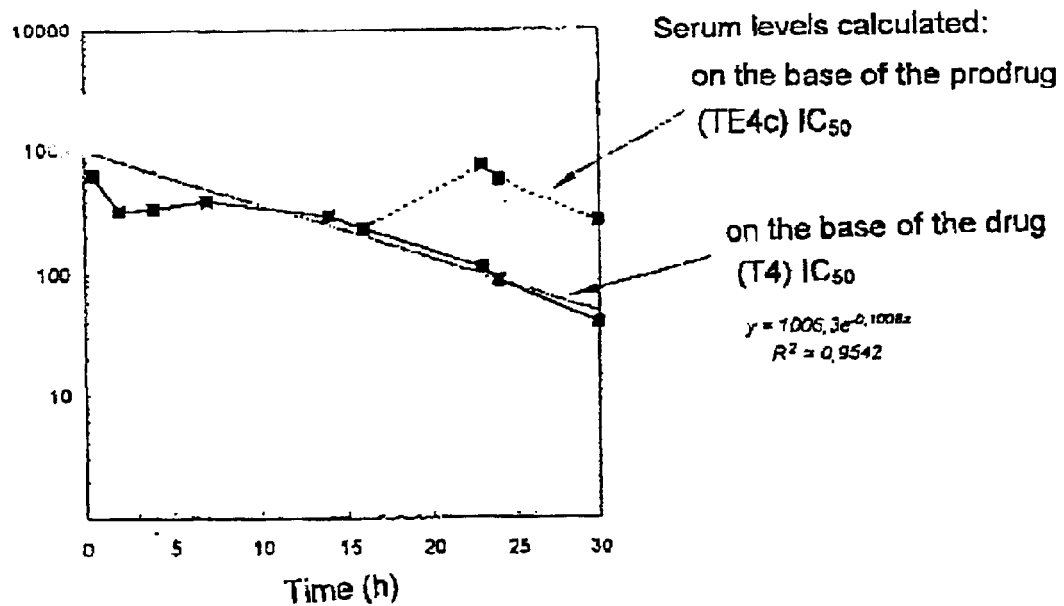

A diphase profile was also observed at higher serum levels and in this case the second peak occurs slightly later (at around 23 hours) as shown in FIGS. 5A and 5B.

Estimation of the Pharmacokinetic Parameters: by Oral Route, $C_0$=1 µg/ml and $t_{1/2}$ at around 10 hours.

Pharmacokinetics of TS3b

TS3b was administered to mice at doses of 50 and 400 mg/kg, respectively by intraperitoneal route and by oral route (approximately $LD_{50}/3$).

Figure 6:
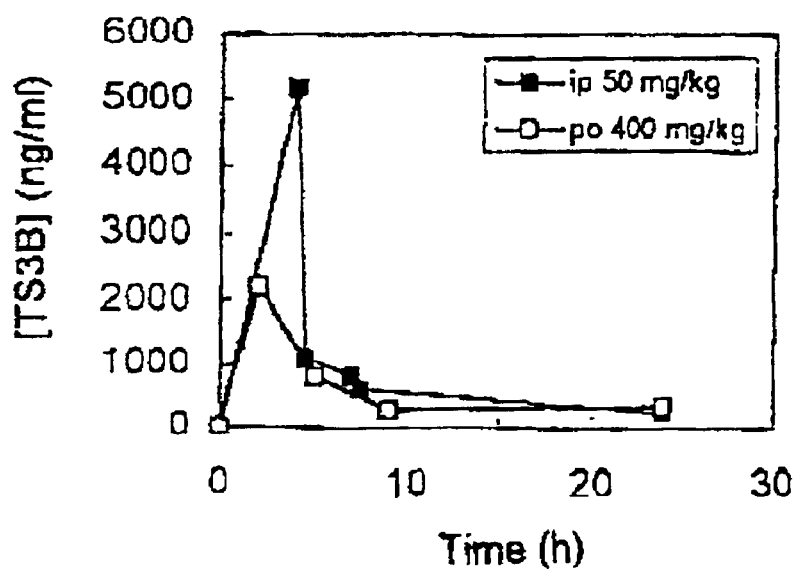

High serum levels are observed forming peaks 2 to 4 hours after the administration of drugs (FIG. 6). The pharmacokinetic parameters were then estimated from the semi-logarithmic representation of the serum concentration (calculated on the basis of the $IC_{50}$ of TS3b as a function of time).

After intra-peritoneal administration at 50 mg/kg, a $C_0$ of 2.75 µg/ml is obtained with $t_{1/2}$ of approximately 6 hours.

By oral route at 400 mg/kg, $C_0$ is 1.8 µg/ml, indicating very high serum levels. The apparent $t_{1/2}$ is 13 hours. Such a difference in the $t_{1/2}$ between the two administration routes could indicate a difference in the metabolization of the prodrug.

The pharmacokinetic profile observed in FIG. 6 could reflect only the first phase of a diphase profile, corresponding to an absorption/distribution phase, such as that observed for the prodrug of thioester type TE4c.

Figure 7:
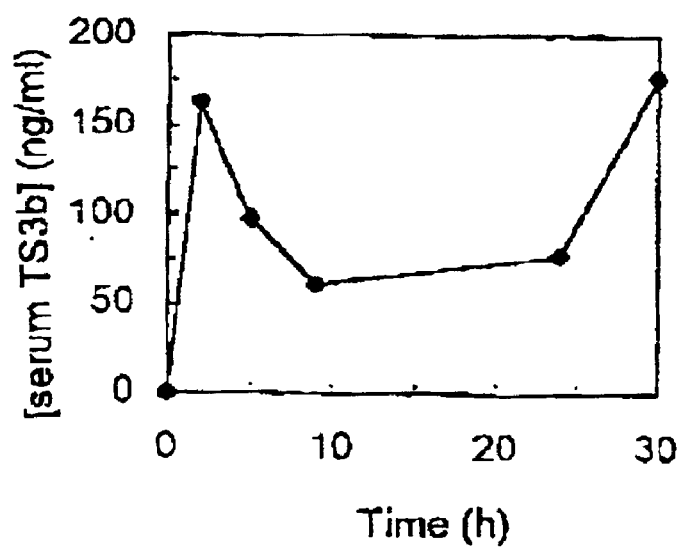

Another series of experiments was carried out to check the existence of a diphase profile, with blood samples taken up to 30 hours after the administration of the drug by ip route (see FIG. 7 which gives the serum concentration of TS3b in ng/ml as a function of time in hours).

It can be observed that a diphase profile is indeed obtained, although incomplete.

The first phase is characterized by a peak at approximately 2 hours with a serum levels decreasing until 10 hours; between 10 and 24 hours, only a slight increase is observed followed by a sharp increase between 24 hours and 30 hours. This probably corresponds to a first phase in which the prodrug is distributed and enters the serum compartment.

This first phase appears less early than for TE4C considered above.

Once in the serum compartment, the conversion of the prodrug into a quaternary compound occurs. Very long term pharmacokinetic experiments must be carried out in order to evaluate the pharmacokinetic parameters of the second phase (i.e. the ionized derivative corresponding to T3) which led to the use of the monkey as a model.

Pharmacokinetic Parameters in the Monkey.

Figure 8A:
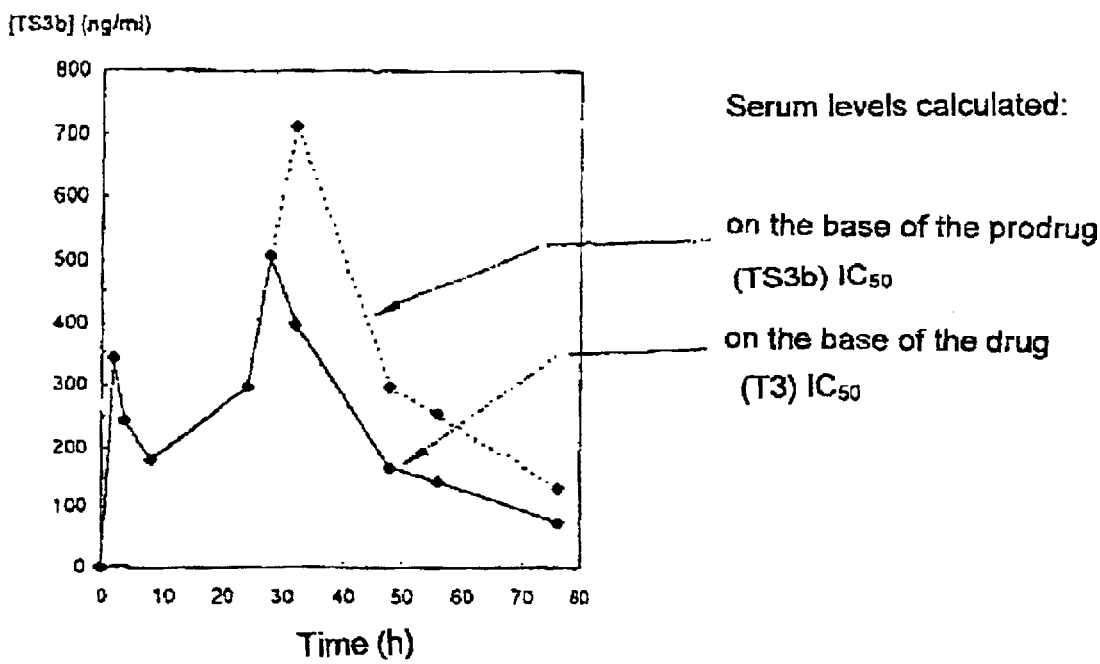
Figure 8B:
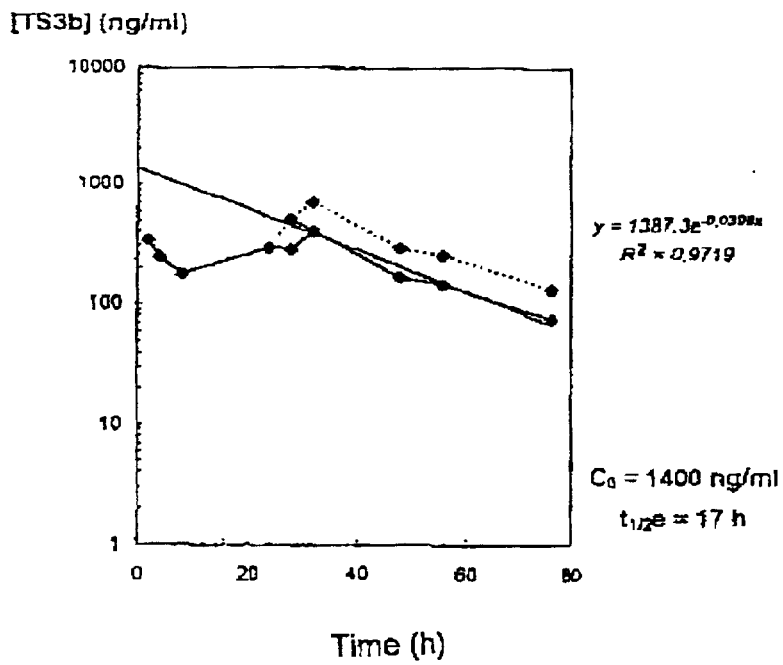

TS3b is administered by intramuscular route to *Macaca fascicularis* monkeys at 4 mg/kg (see FIGS. 8A and 8B which give the concentration in TS3b in ng/ml as a function of time in hours).

Repeated blood samples are taken up to 76 hours and a clear diphase profile is observed.

The first phase very rapidly forms a peak in less than two hours with a serum levels decreasing up to 10 hours, then increasing and forming a peak again at around 30 hours.

As indicated above, this can correspond to the first rapid phase for which the prodrug is distributed and enters the serum compartment.

Once in this compartment, the prodrug converts to quaternary ammonium compounds.

The second phase can then be carried out in order to determine the pharmacokinetic parameters of the ionized derivative corresponding to T3.

If it is considered that the complete conversion to the ionized drug has occurred, the pharmacokinetic profile can be redrawn above on the basis of the $IC_{50}$ of the drug and not on the basis of the prodrug (see FIG. 8A). High serum levels are observed, $C_0$ is 1.4 µg/ml and $t_{1/2}$ around 17 hours.

These results taken together demonstrate the pharmacokinetic properties of the different products appropriate for making use of the different pharmacological activities claimed.

Antimalarial Activity Against *Plasmodium falciparum* in the Aotus Monkey.

3 Aotus monkeys were infected with *P. falciparum* (FVO strain). When the blood parasitemia reached 1% (2 monkeys) or 6% (1 monkey), treatment by intramuscular route at a rate of 2 injections per day of TE4c (2mg/kg), for 8 days, was carried out. In each case, the blood parasitemia was completely eliminated and no further occurrence was observed in the 6 months following the treatment. These results indicate the compound's effective capacity for curing human malaria caused by *P. falciparum*.

Antibabesiasis Activities of the Compounds

The products TE4c, TS3b and P1 were also evaluated in vitro for their activities against Babesia divergens and *B. canis*. In both cases, the compounds TE4c, TS3b and P1 showed themselves to be particularly active ($IC_{50}<20$ nM). These results indicate a strong antibabesia activity for this type of compounds.

What is claimed is:

1. Precursors of drugs with an anti-malarial action, characterized in that they are precursors of quaternary bis-ammonium salts and that they correspond to general formula (I)

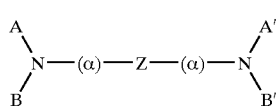

(I)

in which

A and A' are identical to or different from one another and represent either, an $A_1$ and $A'_1$ group respectively, of formula

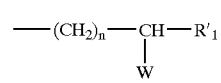

where n is an integer from 2 to 4; $R'_1$ represents a hydrogen atom, a C1 to C5 alkyl radical, optionally substituted by an aryl radical, a hydroxy, an alkoxy, in which the alkyl radical comprizes from 1 to 5 C, or aryloxy; and W represents a halogen atom chosen from chlorine, bromine or iodine, or a nucleofuge group selected from the group consisting of $CH_3$—$C_6H_4$—$SO_3$, $CH_3$—$SO_3$, $CF_3$—$SO_3$, and $NO_2$—$C_6H_4$—$SO_3$ or an $A_2$ group which represents a formyl —CHO radical, or an acetyl —CO—$CH_3$, B and B' are identical to or different from one another and represent either the $B_1$ and $B'_1$ groups respectively, if A and A' represent $A_1$ and $A'_1$ respectively, $B_1$ and $B'_1$ representing an $R_1$ group which has the same definition as $R'_1$ above, but cannot be a hydrogen atom, or the $B_2$ and $B'_2$ groups respectively, if A and A' represent $A_2$, $B_2$, or $B'_2$ being the $R_1$ group as defined above, or a group of formula

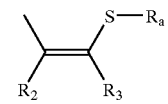

in which —Ra represents an RS— or RCO— group, where R is a linear, branched or cyclic C1 to C6 alkyl radical, optionally substituted by one or more hydroxy, alkoxy or aryloxy group, or an amino group and/or a —COOH or COOM group, where M is a C1 to C3 alkyl; a phenyl or benzyl radical, in which the phenyl radical is optionally substituted by at least one C1 to C5 alkyl or alkoxy radical, these being optionally substituted by an amino group, or by a nitrogenous or oxygenous heterocycle, a —COOH or —COOM group; or a saturated —$CH_2$-heterocycle group, with 5 or 6 elements, nitrogenous and/or oxygenous; $R_2$ represents a hydrogen atom, a C1 to C5 alkyl radical, or a —$CH_2$—COO-alkyl (C1 to C5) group; and $R_3$ represents a hydrogen atom, a C1 to C5 alkyl or alkenyl radical, optionally substituted by —OH, a phosphate group, an alkoxy radical, in which the alkyl radical is C1 to C3, or an aryloxy radical; or an alkyl (or aryl), carbonyloxy group; or also $R_2$ and $R_3$ together form a ring with 5 or 6 carbon atoms; R and $R_3$ can be linked to form a cycle of 5 to 7 atoms (carbon, oxygen, sulphur)

α represents either a single bond, when A and A' represent $A_1$ and $A'_1$: or when A and A' represent $A_2$, i.e. a —CHO or —$COCH_3$ group, and $B_2$ and $B'_2$ represent

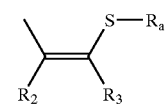

or, when A and A' represent $A_2$ and $B_2$ and $B'_2$ represent $R_1$, a group of formula

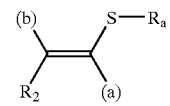

or a group of formula

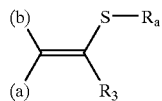

in which (a) represents a bond towards Z and (b) a bond towards the nitrogen atom, Z represents a C6 to C21 alkylene radical, optionally with insertion of one or more multiple bonds, and/or one or more O and/or S heteroatoms, and/or one or more aromatic rings, and the pharmaceutically acceptable salts of these compounds, provided that R'$_1$ does not represent H or a C1 or C2 alkyl radical, when n=3 or 4, R$_1$ represents a C1 to C4 alkyl radical and Z represents a C6 to C10 alkylene radical.

2. Precursors according to claim 1, characterized in that it relates to haloalkylamines, corresponding to general formula (II)

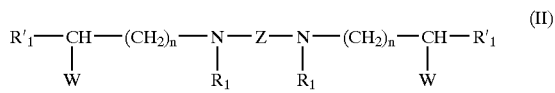

in which R$_1$, R'$_1$, W, n and Z are as defined in claim 1.

3. Precursors according to claim 1, wherein Z represents a CH13 to C21 alkylene radical.

4. Precursors according to claim 3, characterized in that Z represents a —(CH$_2$)$_{16}$— group.

5. Precursors according to claim 2 or 3, characterized in that R$_1$ is a methyl radical.

6. Precursors according to claim 2, characterized in that R$_1$ is a methyl radical and R'$_1$ is either a hydrogen atom, or a methyl radical, and W is a chlorine atom.

7. Precursors according to claim 3, characterized in that they are chosen from N, N'-dimethyl-N,N'-(5-chloropentyl)-1,16-hexadecanediamine hydrochloride, or N, N'-dimethyl-N,N'-(4-chloropentyl)-1,16-hexadecanediamine hydrochloride.

8. Precursor according to claim 1, characterized in that it concerns precursors of thiazolium corresponding to general formula (III):

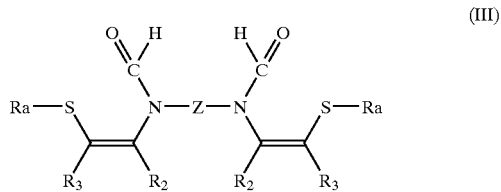

or to general formula (IV)

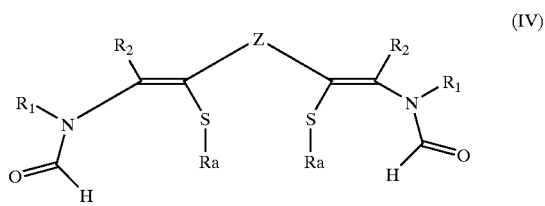

or to general formula (V)

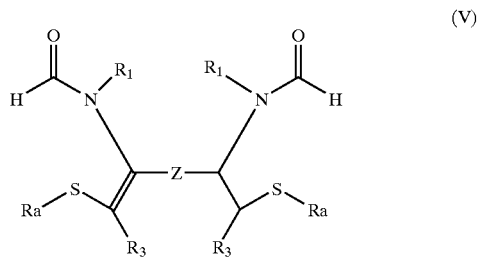

in which R$_a$, R$_1$, R$_2$, and Z are as defined in claim 1.

9. Precursors according to claim 8, characterized in that they correspond to formula III in which R$_a$ represents an RCO— radical.

10. Precursors according to claim 9, characterized in that they are chosen from N,N'-diformyl-N,N'-di[1-methyl-2-S-thiobenzoyl-4-methoxybut-1-enyl]-1,12-diaminododecane, N,N'-diformyl-N,N'-di[1-methyl-2-S-(p-diethylaminomethylphenyl-carboxy)thio-4-methoxybut-1-enyl]-1,12-diaminododecane, N,N'-diformyl-N,N'-di[1-methyl-2-S-(p-morpholino-methylphenylcarboxy)-thio-4-methoxybut-1-enyl]-1,12-diaminododecane, and N,N'-diformyl-N,N'-di[1-methyl-2-S-thiobenzoyl-4-methoxybut-1-enyl]-1,16-diaminohexadecane, and N,N'-diformyl-N,N'-di[1(2-oxo-4,5-dihydro-1,3-oxathian-4-ylidene)ethyl]1,12-diaminododecane.

11. Precursors according to claim 9, characterized in that R$_a$ represents RS—.

12. Precursors according to claim 11, characterized in that they are chosen from N,N'-diformyl-N,N'-di[1-methyl-2-tetrahydrofurfuryl-methyldithio-4-hydroxybut-1-enyl]-1,12-diaminododecane, N,N'-diformyl-N,N'-di[1-methyl-2-propyldithio-4-hydroxybut-1-enyl]-1,12-diaminododecane, N,N'-diformyl-N,N'-di[1-methyl-2-benzyl-dithio-4-hydroxybut-1-enyl]-1, 12-diaminododecane, N,N'-diformyl-N,N'-di[1-methyl-2-(2-hydroxyethyl)-dithio-4-hydroxybut-1-enyl]-1,12-diaminododecane, N,N'-diformyl-N,N'-di[1-methyl-2-propyldithio-4-metho-xybut-1-enyl]-1,12-diaminododecane, and N,N'-diformyl-N,N'-di[1-methyl-2-propyldithio-ethenyl]-1,12-diaminododecane.

13. Precursors according to claim 8, characterized in that they correspond to formula IV and are chosen from 2,17-(N,N'-diformyl-N,N'-dimethyl)diamino-3,16-S-thio-p-methoxybenzoyl-6,13-dioxaoctadeca-2,16-diene, 2,17-(N,N'-diformyl-N,N'-dibenzyl)diamino-3,16-S-thio-p-methoxybenzoyl-6,13-dioxaoctadeca-2,16-diene, ethyl 3,18 (N,N'-diformyl-N,N'-dimethyldiamino-4,17-S-thiobenzoyl-eicosa-3,17-dienedioate (TE12), ethyl 3,18-(N,N'-diformyl-N,N'-dibenzyl)diamino-4,17-S-thiobenzoyl-eicosa-3,17-dienedioate.

14. Precursors according to claim 8, characterized in that they correspond to formula (V) and are chosen from 2,15-(N,N'-diformyl-N,N'-dimethyl)diamino-1,16-S-thiobenzoyl-hexadeca-1,15-diene. 2,15-(N,N'-diformyl-N,N'-dibenzyl)diamino-1,16-S-thio-benzoyl-hexadeca-1,15-diene.

15. The cyclized derivatives corresponding to the precursors of thiazolium of claim 1, said derivatives having general formula (VI)

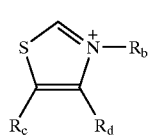
(VI)

in which $R_b$ represents $R_1$ or T, T representing the group of formula

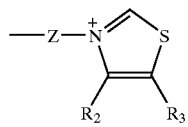

provided that Z does not represent a C6 to C8 alkyene radical, when $R_c$, $R_d$, $R_2$ and $R_3$ represent a methyl radical, $R_d$ represents $R_2$ or P, P representing the group of formula

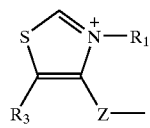

$R_c$ represents $R_3$ or U, U representing the group of formula

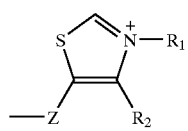

$R_1$, $R_2$, $R_3$ and Z being as defined in claim 1, it being understood that $R_b$=T, if $R_c$=$R_3$ and $R_d$=$R_2$; $R_d$=P, if $R_c$=$R_3$ and $R_b$=$R_1$; and $R_c$=U, if $R_b$=$R_1$, and $R_d$=$R_2$.

16. Process for obtaining precursors of thiazolium of general formula (III) to (IV) according to claim 7, characterized in that it comprises the reaction in basic medium of a thiazole derivative of formula (VI).

17. Process according to claim 16, characterized in that in order to obtain the compounds in which $R_a$=RCO—, a derivative of thiazolium of formula (VI) is reacted with an RCOR' derivative, where R is as defined in claim 1 and R' is a halogen atom, and in order to obtain the compounds in which $R_a$=RS—, said thiazolium derivatives of formula (VI) are reacted with a thiosulphate derivative $RS_2O_3Na$.

18. Process according to claim 15 or 16, characterized in that
in order to obtain the compounds of formula (III) a thiazole derivative suitably substituted with an alkyl dihalide is reacted, under reflux in an organic solvent, the opening of the thiazolium ring then takes place in basic medium, and by the action either of R—COCl, or of $RS_2O_3N_a$,
in order to obtain the compounds of formula IV, which comprize an oxygen in the Z chain, a thiazole derivative of general formula (VII)

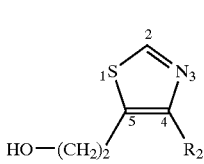
(VII)

is reacted with an alkane dihalide, in basic medium, then the addition of $R_1X$, the reaction medium being advantageously taken to reflux in an organic solvent, in particular alcoholic such as ethanol, for a duration sufficient to obtain the quaternization of the nitrogen atom of the thiazole by fixing $R_1$, the opening of the thiazolium ring then being obtained in basic medium, then by the action either of R—COCl, or of $RS_2O_3Na$, in order to obtain the compounds of formula (IV) not comprizing oxygen in the Z chain, a compound of structure

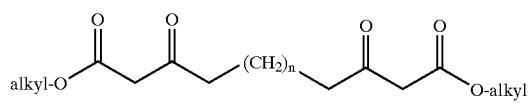

is firstly synthesized by reacting an alkyl acetoacetate with NaH, followed by alkylation, then the addition of a dihalogenoalkane, the compound obtained then being dibrominated, then thioformamide is added and, after reflux for several days, $R_1X$, which leads, after renewed reflux for several days, to a thiazolium, the opening of which is then carried out in basic medium, then the action of R—COCl or of R—$S_2O_3Na$, in order to obtain the compounds of formula (V) not comprizing oxygen in the Z chain, a Z(CO—$CH_2X)_2$ compound is reacted with CH(=S)$NH_2$, then $R_1X$ is added, the opening of the thiazolium ring then being carried out in basic medium, then by adding R—COCl or R—$S_2O_3Na$.

19. Process for obtaining haloalkylamines according to claim 1, characterized in that it comprizes the alkylation of an amino alcohol of formula

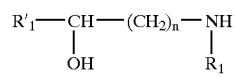

by an alkyl α,ω-dihalide X—Z—X, which leads to a bis-aminoalcohol treated with a compound capable of releasing the W group.

20. Pharmaceutical compositions, characterized in that they contain an effective quantity of at least one precursor as defined in claim 1, or at least one cyclized derivative of general formula (VI):

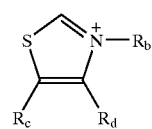
(VI)

in which $R_b$ represents $R_1$ or T, T representing the group of formula:

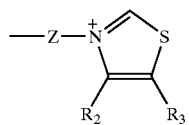

$R_d$ represents $R_2$ or P, P representing the group of formula

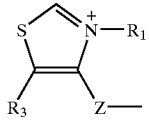

$R_c$ represents $R_3$ or U, U representing the group of formula

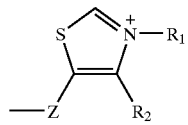

$R_1$, $R_2$, $R_3$ and Z being as defined in claim 1, it being understood that $R_b$=T, if $R_c$=$R_3$ and $R_d$=$R_2$; $R_d$=P, if $R_c$=$R_3$ and $R_b$=$R_1$; and $R_c$=U, if $R_b$=$R_1$, and $R_d$=$R_2$.

in combination with a pharmaceutically inert vehicle.

21. A method of treating at least one of malaria and babesiosis comprising administering to an animal in need of said treatment a quaternary bis-ammonium salt of formula I

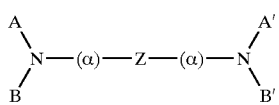

(I)

in which

A and A' are identical to or different from one another and represent either, an $A_1$ and $A'_1$ group respectively, of formula

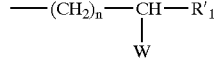

where n is an integer from 2 to 4; $R'_1$ represents a hydrogen atom, a C1 to C5 alkyl radical, optionally substituted by an aryl radical, a hydroxy, an alkoxy, in which the alkyl radical comprizes from 1 to 5 C, or aryloxy; and W represents a halogen atom chosen from chlorine, bromine or iodine, or a nucleofuge group, such as the tosyl $CH_3$—$C_6H_4$—$SO_3$, mesityl $CH_3$—$SO_3$, $CF_3$—$SO_3$, $NO_2$—$C_6H_4$—$SO_3$ radical, or an $A_2$ group which represents a formyl —CHO radical, or an acetyl —CO $CH_3$ radical, B and B' are identical to or different from one another and represent either the $B_1$ and $B'_1$ groups respectively, if A and A' represent $A_1$ and $A'_1$ respectively, $B_1$ and $B'_1$ representing an $R_1$ group which has the same definition as $R'_1$ above, but cannot be a hydrogen atom, or the $B_2$ and $B'_2$ groups respectively, if A and A' represent $A_2$, $B_2$ or $B'_2$ being the $R_1$ group as defined above, or a group of formula

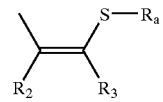

in which —Ra represents an RS— or RCO— group, where R is a linear, branched or cyclic C1 to C6 alkyl radical, optionally substituted by one or more hydroxy, alkoxy or aryloxy group, or an amino group and/or a —COOH or COOM group, where M is a C1 to C3 alkyl; a phenyl or benzyl radical, in which the phenyl radical is optionally substituted by at least one C1 to C5 alkyl or alkoxy radical, these being optionally substituted by an amino group, or by a nitrogenous or oxygenous heterocycle, a —COOH or —COOM group; or a saturated —$CH_2$-heterocycle group, with 5 or 6 elements, nitrogenous and/or oxygenous; $R_2$ represents a hydrogen atom, a C1 to C5 alkyl radical, or a —$CH_2$—COO-alkyl (C1 to C5) group; and $R_3$ represents a hydrogen atom, a C1 to C5 alkyl or alkenyl radical, optionally substituted by —OH, a phosphate group, an alkoxy radical, in which the alkyl radical, in which the alkyl radical is C1 to C3, or an aryloxy radical; or an alkyl (or aryl), carbonyloxy group; or also $R_2$ and $R_3$ together form a ring with 5 or 6 carbon atoms; and R and $R_3$ can be linked to form a cycle of 5 to 7 atoms (carbon, oxygen, sulphur)

α represents either a single bond, when A and A' represent $A_1$ and $A'_1$:
or when A and A' represent $A_2$, i.e. a —CHO or —$COCH_3$ group, and $B_2$ and $B'_2$ represent

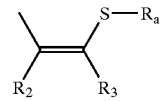

or, when A and A' represent a —CHO group and $B_2$ and $B'_2$ represent $R_1$, a group of formula

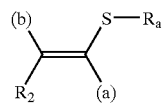

or a group of formula

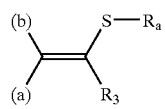

in which (a) represents a bond towards Z and (b) a bond towards the nitrogen atom, Z represents a C6 to C21 alkylene radical, optionally with insertion of one or more multiple bonds, and/or one or more O and/or S heteroatoms, and/or one or more aromatic rings, and the pharmaceutically acceptable salts of these compounds.

22. Pharmaceutical compositions according to claim 20, in a form which may be administered by at least one of the oral route, injectable route, or rectal route.

23. A precursor according to claim 1 wherein said aryl radical is a phenyl radical.

24. A precursor according to claim 21 wherein said aryl radical is a phenyl radical.

25. A precursor according to claim 1 wherein said aryloxy is a phenoxy.

26. A precursor according to claim 21 wherein said aryloxy is a phenoxy.

27. A method according to claim 21 wherein said animal is a man.

* * * * *